(12) United States Patent
Blanton et al.

(10) Patent No.: US 9,986,935 B2
(45) Date of Patent: Jun. 5, 2018

(54) ON-AIRWAY PULMONARY FUNCTION TESTER

(71) Applicant: MGC Diagnostics Corporation, St. Paul, MN (US)

(72) Inventors: David A. Blanton, Humboldt, TN (US); Charles P. Howard, Humboldt, TN (US); Joshua L. Stevenson, St. Paul, MN (US)

(73) Assignee: MGC Diagnostics Corporation, St. Paul, MN (US)

( * ) Notice: Subject to any disclaimer, the term of this patent is extended or adjusted under 35 U.S.C. 154(b) by 782 days.

(21) Appl. No.: 13/927,329

(22) Filed: Jun. 26, 2013

(65) Prior Publication Data
US 2015/0005639 A1    Jan. 1, 2015

(51) Int. Cl.
*A61B 5/08* (2006.01)
*G01N 33/00* (2006.01)
(Continued)

(52) U.S. Cl.
CPC ............ *A61B 5/0873* (2013.01); *A61B 5/082* (2013.01); *A61B 5/085* (2013.01); *A61B 5/0813* (2013.01); *A61B 5/0876* (2013.01); *A61B 5/097* (2013.01); *A61M 16/0057* (2013.01); *A61M 16/206* (2014.02); *B63C 11/22* (2013.01); *G01N 1/2247* (2013.01); *G01N 21/59* (2013.01); *G01N 33/0009* (2013.01)

(58) Field of Classification Search
None
See application file for complete search history.

(56) References Cited

U.S. PATENT DOCUMENTS 5,022,406 A * 6/1991 Tomlinson ............ A61B 5/0813
600/532
5,468,961 A * 11/1995 Gradon ................. A61M 16/16
250/343

(Continued)

FOREIGN PATENT DOCUMENTS

WO    2008095120 A2    8/2008

OTHER PUBLICATIONS

Stoelting et al. 2006 in Handbook of Pharmacology & Physiology in Anesthetic Practice, Stoelting Ed. Lippincott Williams & Wilkins, Chapter 51 p. 51-1 to 51-2.*

(Continued)

*Primary Examiner* — Tse Chen
*Assistant Examiner* — Patrick M Mehl
(74) *Attorney, Agent, or Firm* — Nikolai & Mersereau, P.A.; Thomas J. Nikolai

(57) ABSTRACT

A compact, on-airway, respiratory gas analyzer for performing pulmonary function tests incorporates an IR spectroscopy light guide having a curved, rather than linear, sample chamber that lies transverse to a direction of respiratory gas flow. Cooperating with the sample chamber is an impact plate that functions to steer respiratory and test gases impinging on the impact plate into the curved sample chamber. A source of IR energy is at one end of the sample chamber and an electro-optical sensor responsive to IR energy is disposed at an opposite end of the chamber. The respiratory gas analyzer also includes gas flow paths and valving for carrying out lung capacity and lung diffusion tests.

12 Claims, 22 Drawing Sheets

(51) Int. Cl.

| | |
|---|---|
| *G01N 21/59* | (2006.01) |
| *G01N 1/22* | (2006.01) |
| *A61B 5/087* | (2006.01) |
| *A61M 16/20* | (2006.01) |
| *A61B 5/085* | (2006.01) |
| *A61B 5/097* | (2006.01) |
| *B63C 11/22* | (2006.01) |
| *A61M 16/00* | (2006.01) |

(56) References Cited

U.S. PATENT DOCUMENTS

| | | | | |
|---|---|---|---|---|
| 2005/0180889 | A1* | 8/2005 | Martin | G01N 21/05 422/83 |
| 2005/0197589 | A1* | 9/2005 | Kline | A61B 5/083 600/532 |
| 2008/0029462 | A1* | 2/2008 | Huymann | C02F 1/34 210/748.01 |
| 2009/0227887 | A1* | 9/2009 | Howard | A61B 5/0833 600/531 |
| 2010/0252046 | A1* | 10/2010 | Dahlstrom | A61M 16/01 128/205.24 |
| 2011/0009762 | A1* | 1/2011 | Eichler | A61B 5/085 600/532 |
| 2011/0098589 | A1* | 4/2011 | Clemensen | A61B 5/0813 600/532 |
| 2011/0259452 | A1* | 10/2011 | Carter | G01N 1/2208 137/565.13 |
| 2012/0253218 | A1* | 10/2012 | Rosenthal | A61B 5/091 600/538 |

OTHER PUBLICATIONS

Takatori et al. 2011 Conf.Proc.IEEE Eng.Med.Biol.Soc. 2011:1189-92.*

Snow, Michael G.; "Chapter 45: Assessment of Lung Volumes"; Foundations of Respiratory Care, pp. 449-455.

Schlegelmilch, Rolf M.; Kramme, Rudiger.; "Part B/8. Pulmonary Testing", Functional Diagnostics Devices, Springer Handbook of Medical Terminology, 2012, XLVI, pp. 95-117.

Brown, D; Leith, D.E.; Enright, P.L.: "Multiple Breath Helium Dilution Measurement of Lung Volumes in Adults", Copyright 1998, ERS Journals Ltd. European Respiratory Journal, pp. 246-255.

Gildea, Thomas R., McCarthy, Kevin: "Pulmonary Function Testing", Copyright 2000-2011, The Cleveland Clinic Foundation.

* cited by examiner

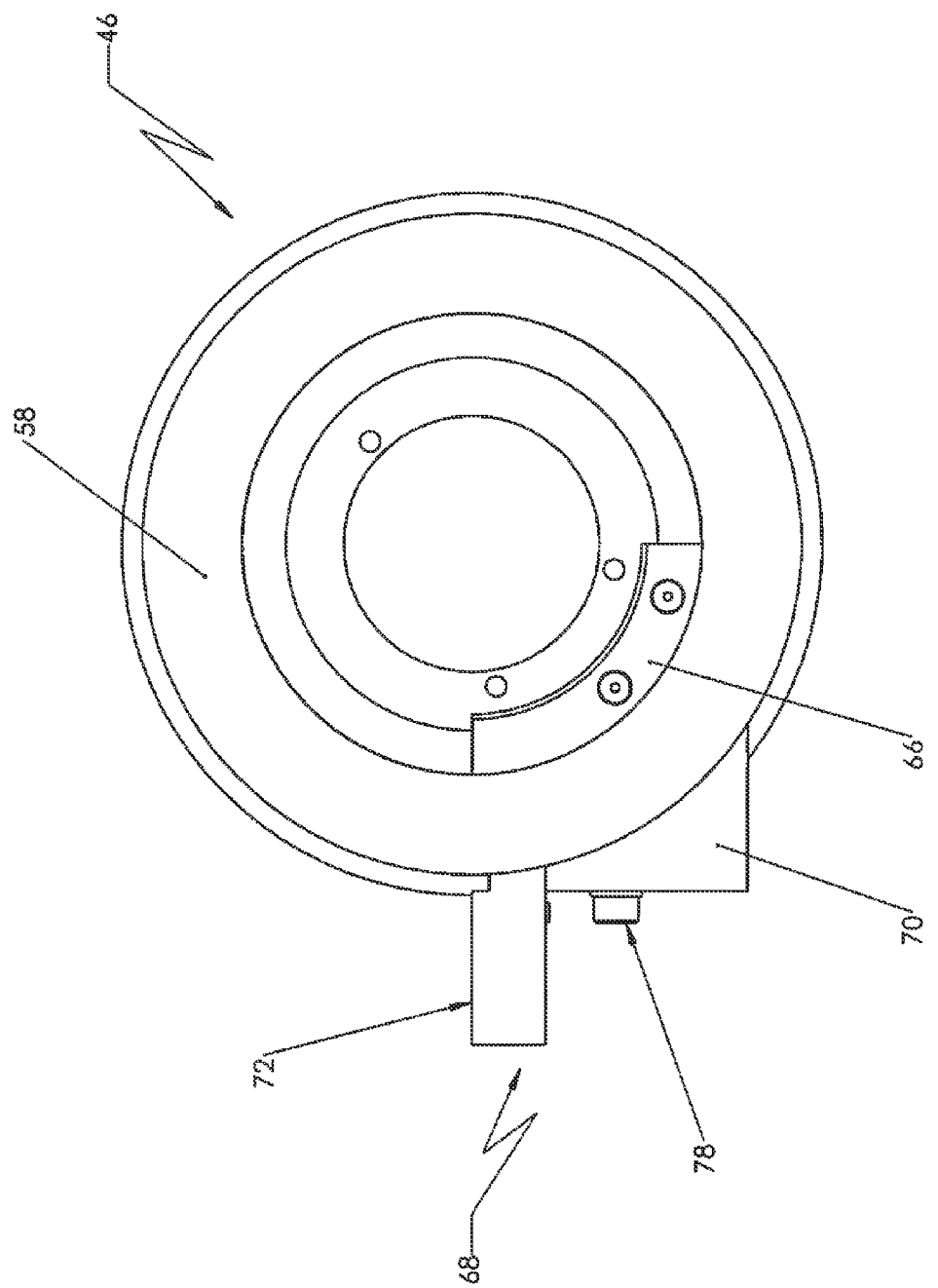

ON-AIRWAY PULMONARY FUNCTION TESTER

BACKGROUND OF THE INVENTION

I. Field of the Invention

This invention relates generally to a diagnostic instrument for assessing lung function, and more particularly to a small, lightweight, on-airway instrument for assessing pulmonary performance of a patient.

II. Description of the Prior Art

Pulmonary function testing is a valuable tool for evaluating a patient's respiratory system. Pulmonary function tests (PFTs) is a generic term used to indicate a battery of studies of maneuvers that may be performed using standardized equipment to measure lung function. PFTs may include simple screening spirometry, formal lung volume measurement, diffusing capacity for carbon monoxide and arterial blood gases.

PFTs are noninvasive diagnostic tests that provide measurable feedback about the function of the lungs. By assessing lung volumes, capacities, rates of flow and gas exchange, PFTs provide information that, when evaluated by a medical professional, can help diagnose certain lung disorders.

A normally-functioning pulmonary system operates on many different levels to insure adequate balance. One of the primary functions of the pulmonary system is ventilation, i.e., the movement of air into and out of the lungs.

Various medical conditions can interfere with ventilation. Such conditions are typically classified as being "restrictive" or "obstructive". An obstructive condition occurs when air has difficulty flowing out of the lungs due to resistance, causing a decrease flow of air. A restrictive condition occurs when the chest muscles are unable to expand adequately, creating a disruption in airflow. PFTs involve several different procedures for obtaining values that can be compared to standards for a large population for comparison purposes. Some of the more common values typically measured during PFT include:

| PARAMETER | DESCRIPTION | UNIT |
| --- | --- | --- |
| FVC | Forced Vital Capacity | L |
| FEV1 | Forced Expiratory Volume in 1 s | L |
| FEV1/FVC | FEV1 in % of FVC | % |
| PEF | Peak Expiratory Flow | L/s |
| FIV1 | Forced Inspiratory Volume in 1 s | L |
| FRC | Functional Residual Capacity | L |
| $D_{LCO}$ | Diffusing Capacity | |
| MIP | Maximum Inspiratory Pressure | MMHg |
| MEP | Maximum Expiratory Pressure | MMHg |

The spirometry measurements typically require a voluntary maneuver in which a patient inhales maximally from vital respiration to total lung capacity and then rapidly exhales to the fullest extent until no further volume is exhaled at residual volume. This maneuver may be performed in a forced manner to generate forced vital capacity (FVC) or in a more relaxed manner to generate a slow vital capacity (SVC). Various types of spirometers are known in the art for directly measuring the volume of air displaced or that measures airflow by a flow-sensing device, such as a pneumotachometer. Presently, most PFT laboratories use a microprocessor-driven pneumotachometer to measure airflow directly and from which volume can be mathematically derived. Because spirometry is an expiratory maneuver, it measures exhaled volume or vital capacity, but does not measure residual volume, functional residual capacity (resting lung volume), or total lung capacity. Vital capacity is a simple measure of lung volume that is usually reduced in patients suffering from restrictive disorders.

Other pulmonary function tests are needed to measure total lung capacity, which is derived from the addition of functional residual capacity to inspiratory capacity obtained from spirometry. FRC is usually measured by a gas dilution technique or body plethysmography. Gas dilution techniques are based on a simple principle, are widely used and provide a good measurement of all air in the lungs that communicates with the airways. Lung volume measurements obtained using gas dilution techniques either used closed-circuit helium dilution or open-circuit nitrogen washout. In the nitrogen-washout technique, a patient is made to breathe 100% oxygen until all of the nitrogen theretofore in the lungs is washed out. The exhaled volume and the nitrogen concentration in that volume are measured. The difference in nitrogen volume at the initial concentration and the final exhaled concentration allows a calculation of the intrathoracic volume, FRC.

Another important factor in carrying out a PFT is to assess the diffusing capacity of the lungs. It is a measure of the ability of the lungs to transfer oxygen to the blood and to remove $CO_2$ therefrom.

Generally speaking, all methods for measuring diffusing capacity in clinical practice today rely on measuring the rate of carbon monoxide (CO) uptake and estimating carbon monoxide driving pressure. The most widely used and standardized technique is the single-breathe breath-holding technique. In this procedure, a patient inhales a known volume of test gas that usually contains 0.3% methane, 0.3% carbon monoxide, 21% oxygen and the remainder nitrogen. This test gas is inhaled and the patient holds his/her breath for 10 seconds. The patient then exhales to first wash out the mechanical and anatomic dead space and then an alveolar sample is collected. $D_{LCO}$ is then calculated from the total volume of the lung, the breath hold time and the initial and final alveolar concentrations of CO. The exhaled methane concentration is used to calculate a single breath estimate of total lung capacity and initial alveolar concentration of CO.

Almost all current systems for performing PFTs and especially lung volume and lung diffusion capability use a "side streaming" sensor apparatus in which respiratory gas samples are drawn from an airway mouthpiece and conveyed through a sampling tube to a sensor located distant from the sampling site, usually with the aid of a vacuum pump. When it is recognized that lung diffusion measurements (DLCO) involve only small concentrations, it is necessary to have reasonably long path lengths in a non-dispersive infrared (NDIR) system to yield good resolution down to, say, 30 ppm. In that both CO and $CH_4$ are weak absorbers of infrared energy, it is therefore impossible to obtain any reasonable absorption differences in the absence of a long path length. Also in conducting a DLCO measurement, the speed of response is a major factor to obtain good integrals for the gaseous volumes. A very high flow is needed to purge down the side streaming system if a reasonable response is to be achieved. A flow of several hundred cubic centimeters per minute is typically required and this removes a high volume of gas from the patient's circuit, thus creating an artificial breathing environment for the patient. In addition, with this high flow, it is necessary to create quite high vacuums downstream of the analyzer to pull this amount of flow through small bore lines which are necessary to preserve waveform. This results in a loop pressure much below atmospheric. This low pressure directly affects the partial pressure of the gases being measured, CO and $CH_4$, and further reduces resolution.

The "side streaming" type of measurement apparatus also involves issue relating to water removal, temperature and humidity differences at the sampling site and measurement/sensing site, unwanted mixing of a current sample with previous samples as the current sample is being drawn through the sample tube, variability in the pressure drop across the tubing and the introduction of a phase delay between the sample time and the measurement/sensing of that sample. The phase delay is attributable to the fact that flow is measured instantaneously at the patient's mouth with a pneumotach and the measured pressure differential from the pneumotach is transmitted at the speed of sound. The analysis for a component level at any given flow necessarily lags behind the flow and has to be allowed for in the calibration and software. To reduce the lag, the flow can be increased but this results in higher vacuum in the cell and more patient interference.

More recently, efforts have been made to develop "mainstream" respiratory gas sensors where the measurement/sensing takes place immediately adjacent the subject's mouthpiece, i.e., directly on the airway as a way of obviating the aforementioned problems with sidestream systems. It is accordingly a principal purpose of the present invention to provide an improved mainstream analyzer involving an on-airway construction that allows for a relatively long sample chamber path length and much greater resolution than can be achieved with side streaming systems and which does so without sacrificing pressure drop and distortion of the patient circuit.

It is a further object of the invention to provide an improved mainstream respiratory gas analyzer system offering an improved speed of response over what can be achieved using side streaming.

Yet another object of the invention is to provide a mainstream respiratory gas analyzer in which water vapor is managed rather than removed.

SUMMARY OF THE INVENTION

The present invention is directed to an instrument for use in carrying out a variety of PFTs in which a pitot tube based pneumotachograph of known construction is used in combination with a uniquely designed respiratory gas analyzer that incorporates an arcuate light transmissive path between a light source and a detector module that provides an on-airway device for facilitating both spirometric measurements and a means for measuring FRC via oxygen washout and lung diffusing capacity, $D_{LCO}$. The respiratory gas analyzer comprises a circularly curved light guide member of C-shaped cross-section that is supported on an adapter plate having a centrally located aperture over which a tubular pneumotachograph is adapted to be mounted. The light guide is positioned concentrically with the aperture and has a light reflective interior surface. Centered within the circularly curved light guide member is an impact plate that is positioned in longitudinal alignment with the aperture in the adapter plate and is operative to direct respiratory gases passing through the aperture and impinging on the impact plate into the light guide member. An IR emitter is operatively placed at one end of the light guide member and a photodetector is operatively located at an opposite end thereof. The photo-detector is capable of responding to light wavelengths at which at least one of CO, $CO_2$, and $CH_4$ is highly absorptive.

The respiratory gas analyzer also incorporates valving and associated pathways for selectively blocking and allowing inspiration of air or test gases and the expiration of gases from the lungs.

The combination of the pneumotachograph and on-airway the respiratory gas analyzer is thus able to perform volume and pressure measurements as well as conducting diffusion capacity measurements and FRC evaluations.

The foregoing features and advantages of the invention will become apparent to persons skilled in the art from the following detailed description of a preferred embodiment, especially when considered in conjunction with the accompanying drawings in which like numerals in the several views refer to corresponding parts.

DESCRIPTION OF THE DRAWINGS

FIG. 6C is a side elevation of the light guide member with light holder and quad sensor mount installed;

DESCRIPTION OF THE PREFERRED EMBODIMENT

Figure 1:
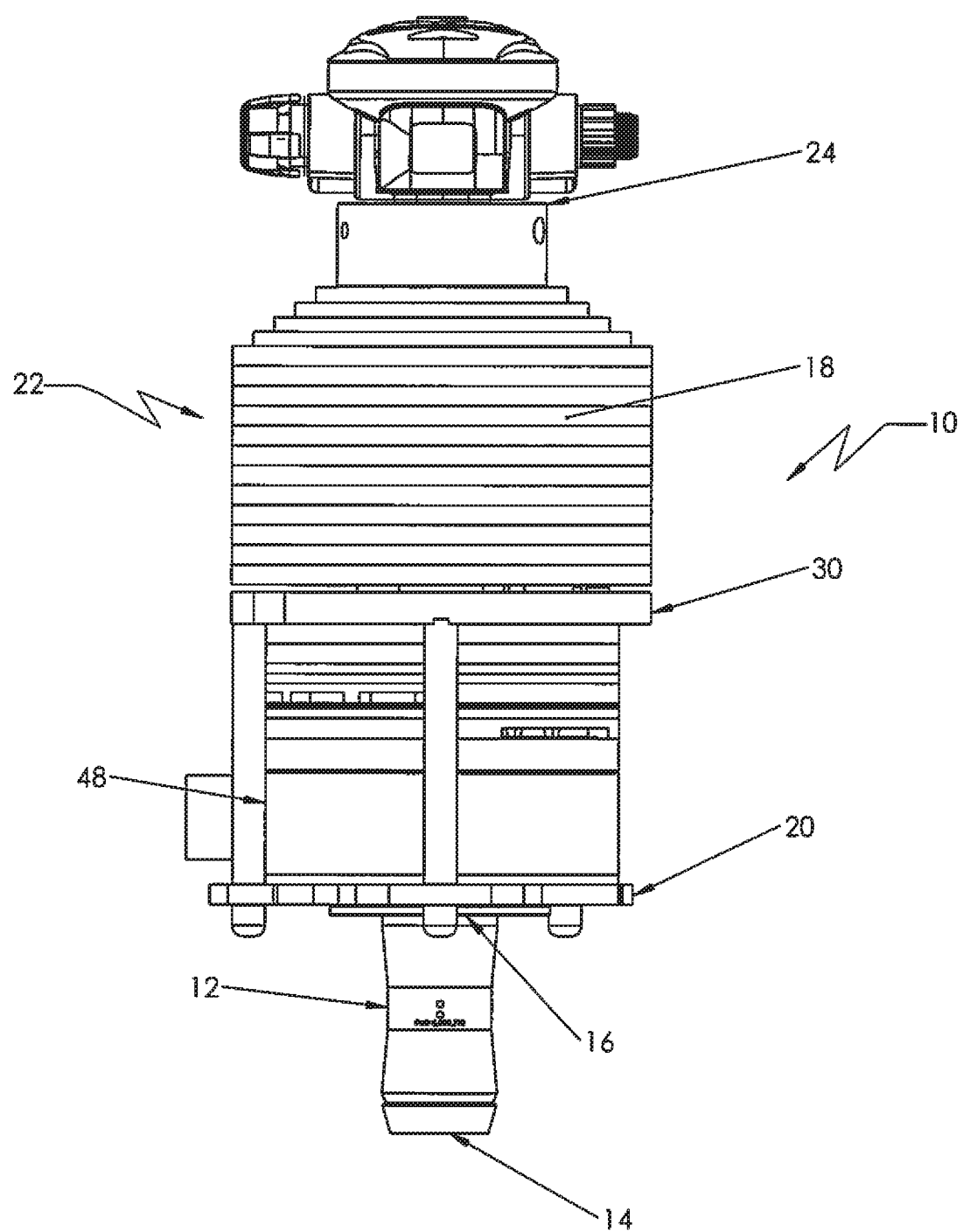
FIG. 1 is a side elevation of a combination of a pneumotach and the on-airway respiratory gas analyzer for performing PFTs.

This description of the preferred embodiments is intended to be read in connection with the accompanying drawings, which are to be considered part of the entire written description of this invention. In the description, relative terms such as "lower", "upper", "horizontal", "vertical", "above", "below", "up", "down", "top" and "bottom" as well as derivatives thereof (e.g., "horizontally", "downwardly", "upwardly", etc.) should be construed to refer to the orientation as then described or as shown in the drawings under discussion. These relative terms are for convenience of description and do not require that the apparatus be constructed or operated in a particular orientation. Terms such as "connected", "connecting", "attached", "attaching", "join" and "joining" are used interchangeably and refer to one structure or surface being secured to another structure or surface or integrally fabricated in one piece, unless expressively described otherwise.

Turning first to FIG. 1, there is indicated generally by numeral 10 a composite assembly of an on-airway device useful in conducting PFTs. It is seen to comprise a pneumotachometer 12 having a mouthpiece 14 and an output end 16 snapped fitted onto a cylindrical, annular boss 19 (FIG. 2) that is integrally formed with an adapter clamp ring 20 of a prototype model of a respiratory gas analyzer assembly indicated generally by numeral 22.

The pneumotachograph 12 is preferably of the type fully described in the Norlien et al. U.S. Pat. No. 5,038,773, the contents of which are hereby incorporated by reference as is fully described herein. The pneumotachograph 12 is capable of accurately measuring respiratory flows and pressures and since volume can be derived by integration of the flow signal, the pneumotach 12 is capable of performing many of the functions of conventional spirometers. Thus, such important parameters as FVC, $FEV_1$, PEF and lung volumes that can be measured directly with a spirometer including tidal volume $V_T$, inspiratory capacity $I_C$, inspiratory reserve volume IRV, expiratory reserve volume ERV, vital capacity VC, maximal inspiratory pressure MIP and maximal expiratory pressure MEP can be derived from a pneumotach. However, since the residual volume cannot be exhaled, the residual volume, functional residual capacity, and the total lung capacity must be measured using indirect methods. There are three indirect techniques to measure these lung volumes, namely, helium or methane dilution, nitrogen washout and body plethysmography. As will be explained in greater detail below, the respiratory gas analyzer 22 adds to the spirometry data information relating to the diffusing capacity of the lungs ($D_{LCO}$) and the functional residual capacity (FRC) obtained using nitrogen washout procedure. In that the pneumotachograph 12 construction and mode of operation are fully described in the aforereferenced '773 patent, nothing further need to be said about it. The remainder of the specification will be devoted to explaining the construction and mode of operation of the prototype on-airway respiratory gas analyzer 22.

Referring to FIGS. 2-5, the respiratory gas analyzer 22 is illustrated with the shroud 18 of FIG. 1 removed. It is seen to comprise an adapter sleeve 24 that allows a conventional scuba demand valve 25 associated with a tank of a pressurized gas or gas mixture (schematically shown in FIG. 17) to be coupled to the respiratory gas analyzer 22. The scuba demand valve operates in a conventional manner to reduce the pressure of the gas reaching the respiratory gas analyzer from about 130 psi in the supply tank to ambient pressure. Inside of the demand valve is a diaphragm that is subject to equal forces of ambient air pressure on one side and air pressure from a breathing subject on the other side. Breathing in from a mouthpiece reduces the air pressure on one side of the diaphragm such that atmospheric pressure is able to push the diaphragm in, opening the intake valve. When a person stops inhaling, the pressure balances and the valve closes. Thus, a test gas in a tank becomes available to the patient only upon his or her inhaling.

Figure 3:
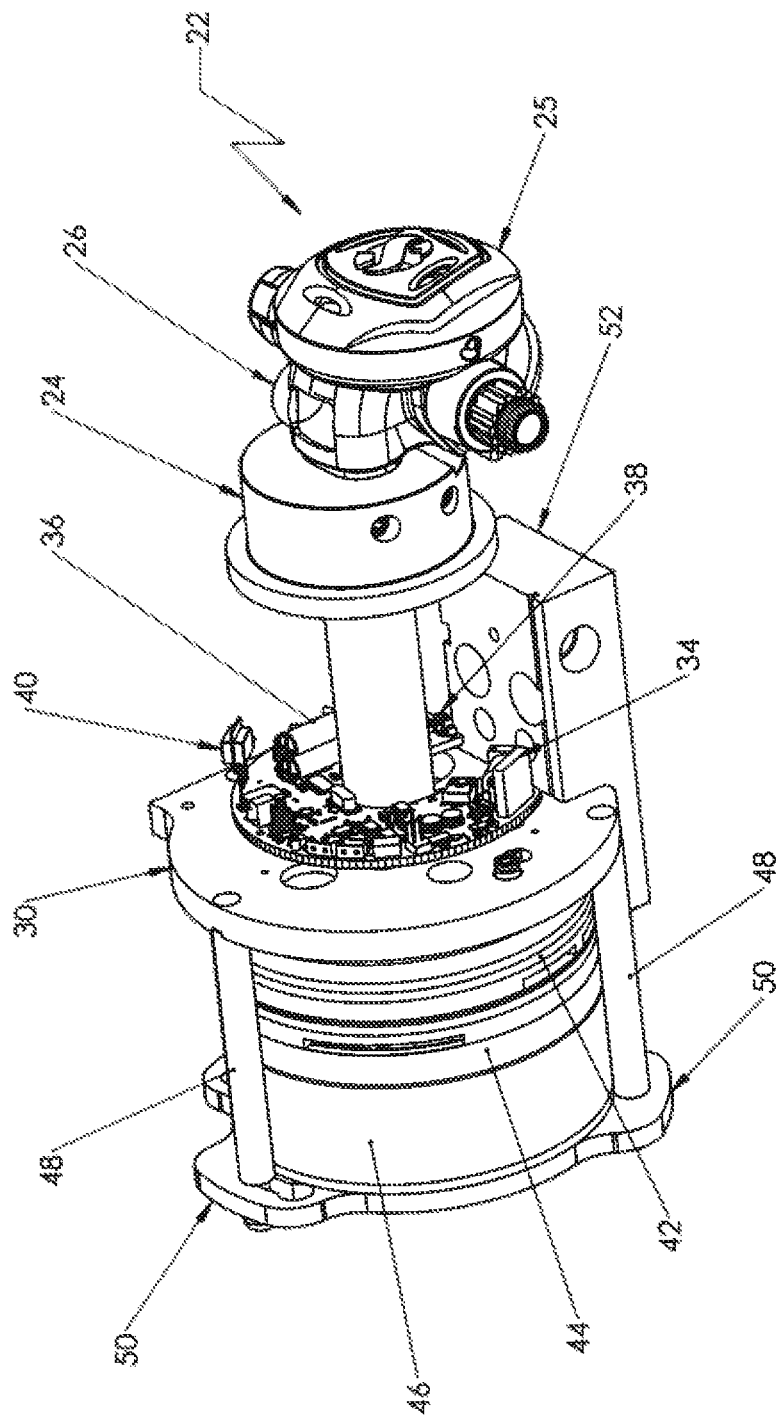
FIG. 3 is a perspective view of the gas analyzer of FIG. 2.
Figure 4:
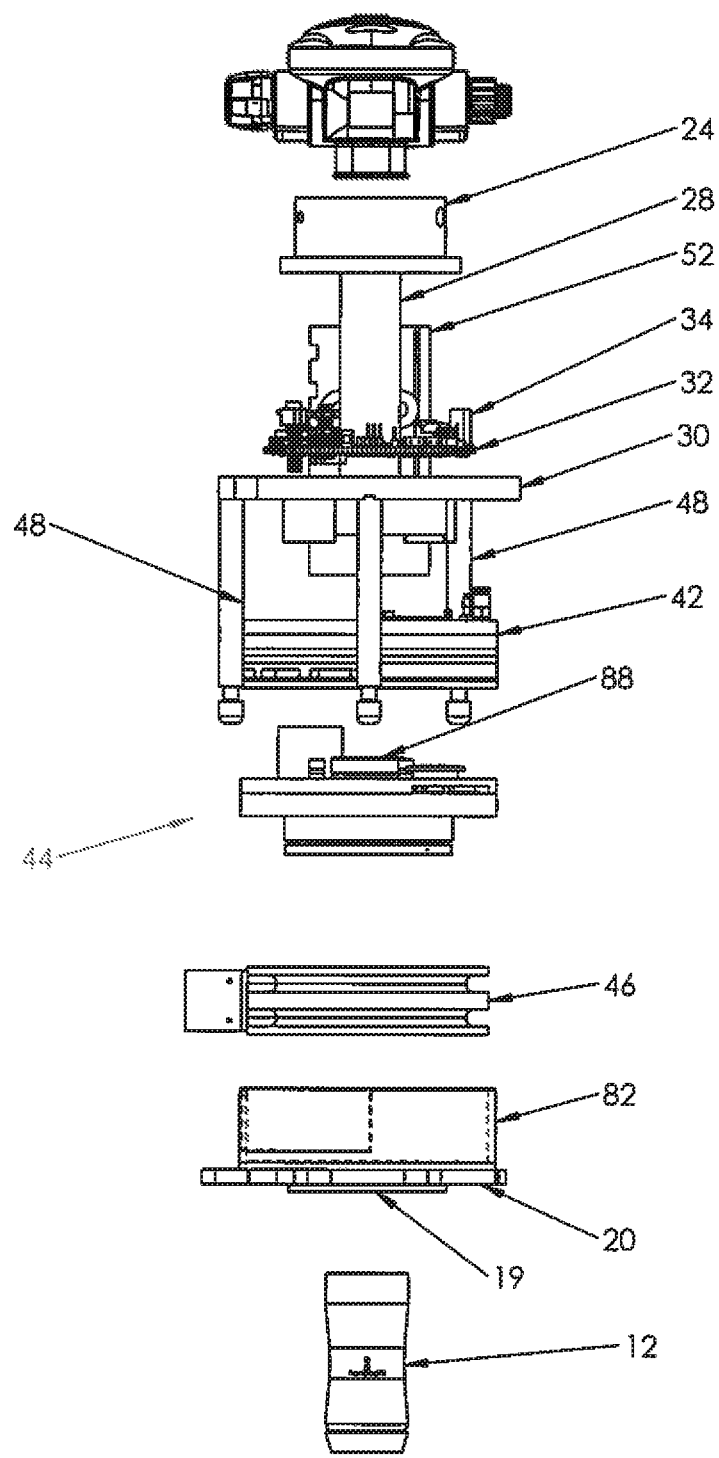
FIG. 4 is an exploded side view of the prototype gas analyzer.

As seen in FIGS. 3 and 4, the scuba demand valve adapter 24 has a central aperture 26 and fitted into this aperture is a tube 28 having its lower end fitted into a manifold mounting plate member 30. The tube has a relatively short length and narrow lumen so as to exhibit a very small volume, which is important where blending of expired air and the test gas is to be avoided.

Partially surrounding the circumference of the tube 28 is a round printed circuit board 32 populated with electronic components including a battery power supply 34, solenoid valves 36, pressure sensors 38, emitter power regulator 40, a microprocessor, as well as other solid-state components for completing the circuitry needed to open and close control valves and to signal process the information derived from IR detectors used for measuring the concentrations of respiratory gases and the constituents of test gases to which the respiratory gas analyzer 22 may be subjected during the course of a PFT procedure.

Sandwiched between and held in place by a clamping arrangement comprising the manifold mounting disk 30 and the adapter ring 20 is an inspiratory chamber 42, an expiratory chamber 44 and a light guide member 46. In the prototype model illustrated, tie rods 48 pass through lobes 50 integrally formed on the adapter plate 20 and the opposed ends screw into threaded bores of the adapter mounting plate 30 to effect clamping. A mounting adapter 52 is also fastened to the plate 30 and it has a series of apertures formed therein allowing the assembly 22 to be conveniently affixed to an existing type of support arm used to suspend PFT equipment at a convenient location proximate the mouth of a subject upon whom the testing is to be run. It is to be recognized that in fabricating the prototype gas analyzer depicted in the drawings, it has been found convenient to fabricate same from plastic disks which could be readily fabricated and modified as necessary and then clamped together to form a composite body with internal pathways and valving. It is expected that production versions of the on-airway pulmonary function tester will be fabricated using a more expensive CNC machining center whereby an aluminum block or other material can be machined to provide the functionality of the prototype being described herein.

Figure 5:
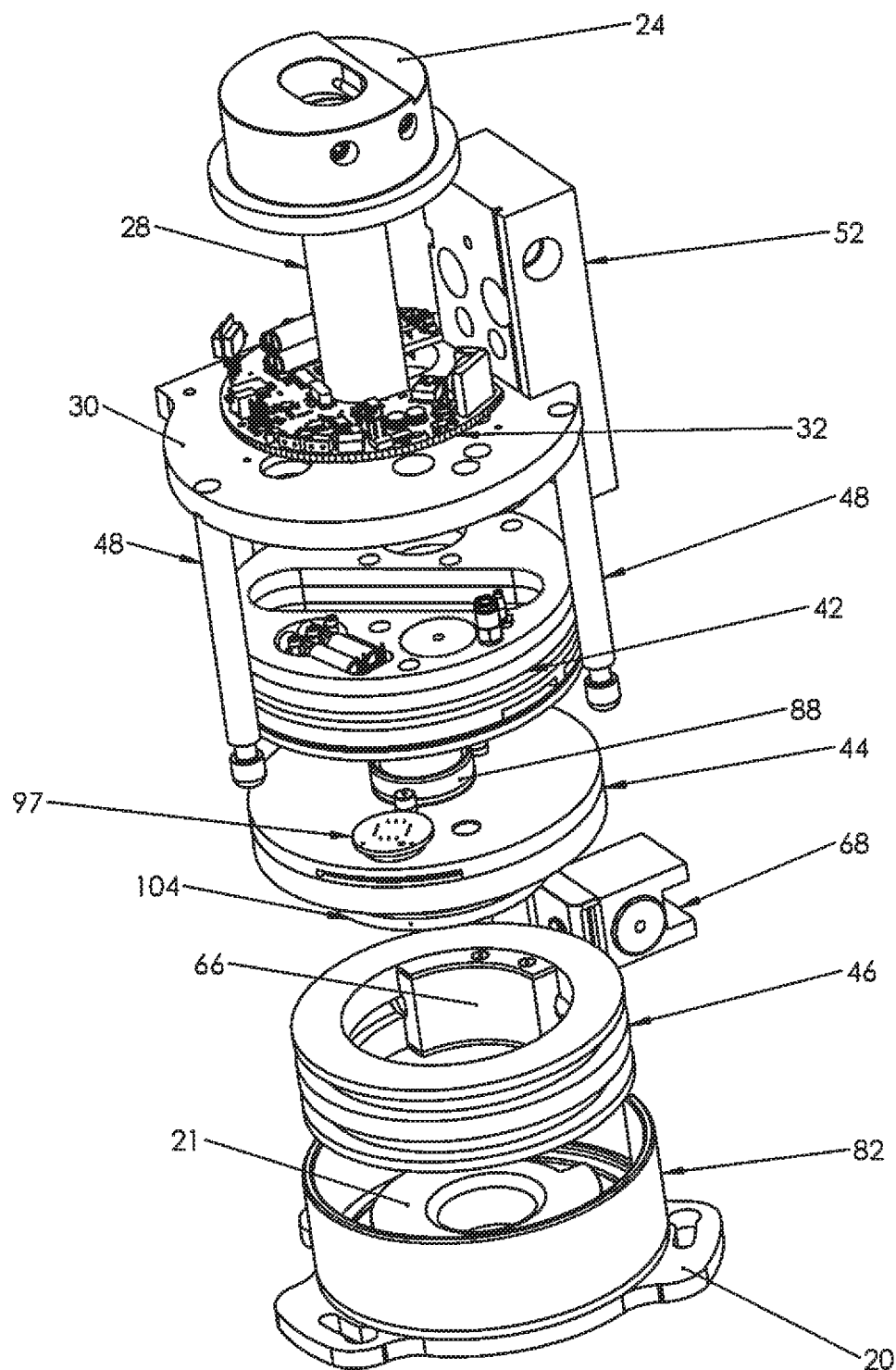
FIG. 5 is an exploded perspective of the prototype gas analyzer.
Figure 6A:
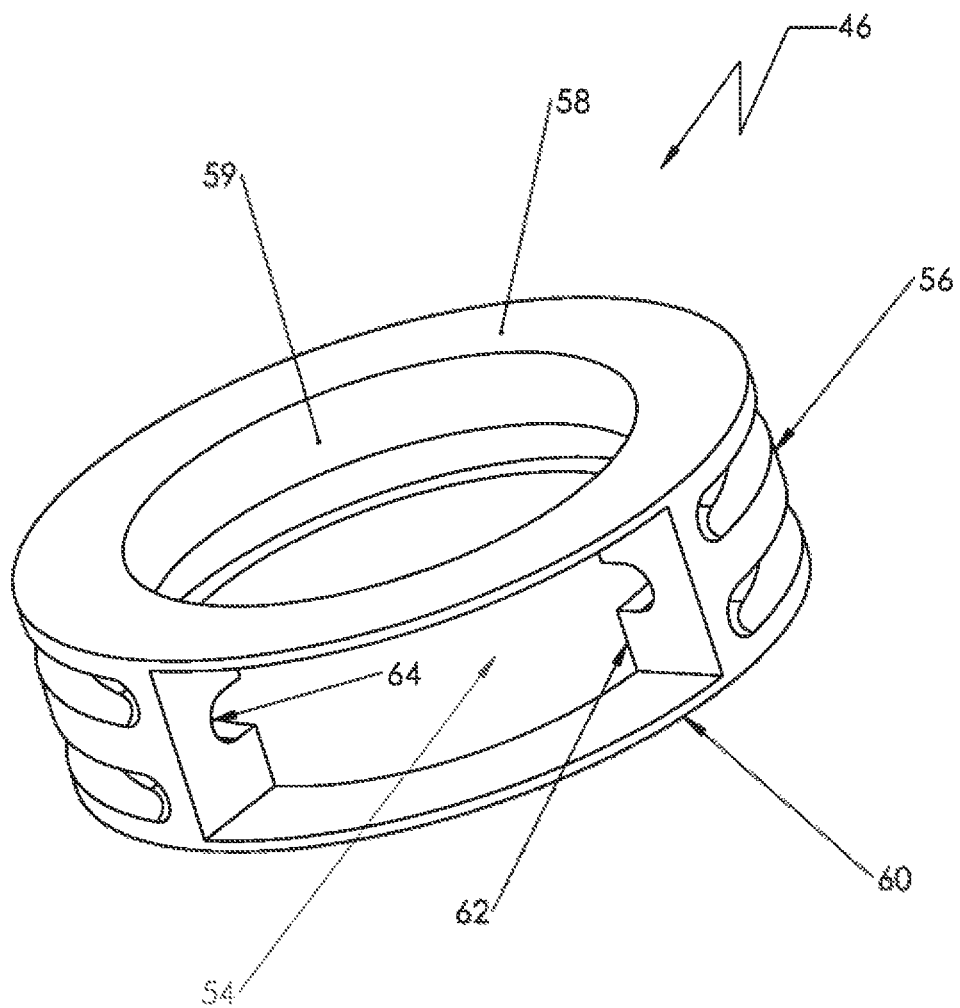
FIG. 6A is a perspective view of the light guide member used in the assembly of FIG. 5.

FIG. 6A is an enlarged perspective view of the light guide member 46. It comprises a molded, thermally conductive plastic or metal cylinder having a generally rectangular window 54 formed through the sidewall 56 thereof between an upper toroidal surface 58 and a lower toroidal surface 60. Formed circumferentially in an inner surface 62 of the sidewall 56 is a generally C-shaped groove 64, the surface of which is provided a highly reflective material, preferably a polished gold. Gold is IR non-absorptive and tends not to tarnish during use. Since gold does not absorb IR energy readily and thus provides an efficient conduit for IR energy. As is more clearly seen in FIG. 5, the opening or window 54 receives a light guide insert 66 therein for containing a small incandescent emitter so as to aim its emitted broad band light waves into one end of the C-shaped groove 64. Without limitation, the C-shaped groove may span an arc in a range from 180° to about 240°. Also affixed to the light holder 66 is a quad sensor subassembly, indicated generally by numeral 68 in the perspective view of FIG. 6B. That subassembly comprises a generally rectangular block 70 of a suitable plastic atop of which is mounted a transparent cover member 72. Beneath the cover member is disposed a plate of high thermal conductivity, preferably aluminum. The plate is identified by numeral 74 and formed through its thickness dimension is an aperture in which is fitted a quad sensor element 76.

The quad sensor element is preferably a purchased item available from Dexter Research Center of Dexter, Mich. Its Model ST60 Quad is a four-channel, silicone-based thermopile detector in a TO-5 package. It is well suited for gas analysis in that by fitting each of its four windows with suitable light filters, that device can be used to detect carbon monoxide, carbon dioxide and methane, which are test gases frequently used in carrying out PFTs. The fourth window can serve as a reference for insuring consistent measurement within nominal tolerances ranges.

When appropriately mounted in the thermally conductive layer 74 and with the block fitted into the member 66 and held by throughbolt 78 (FIG. 6C), the thermopile sensor elements in the quad sensor 76 are exposed to IR energy originating from the emitter and traversing the circular C-shaped reflectively coated groove 64 in the light guide member 46. The wattage of the emitter is such that its heat is sufficient to prevent condensation in the light guide. That is to say, the emitter provides sufficient heat to the arcuate gas sampling chamber so that its temperature remains above the dew point of the expired gas flow. Rather than using the incandescent source to heat the light guide so as eliminate moisture condensation, a separate heating element could also be used.

Figure 6B:
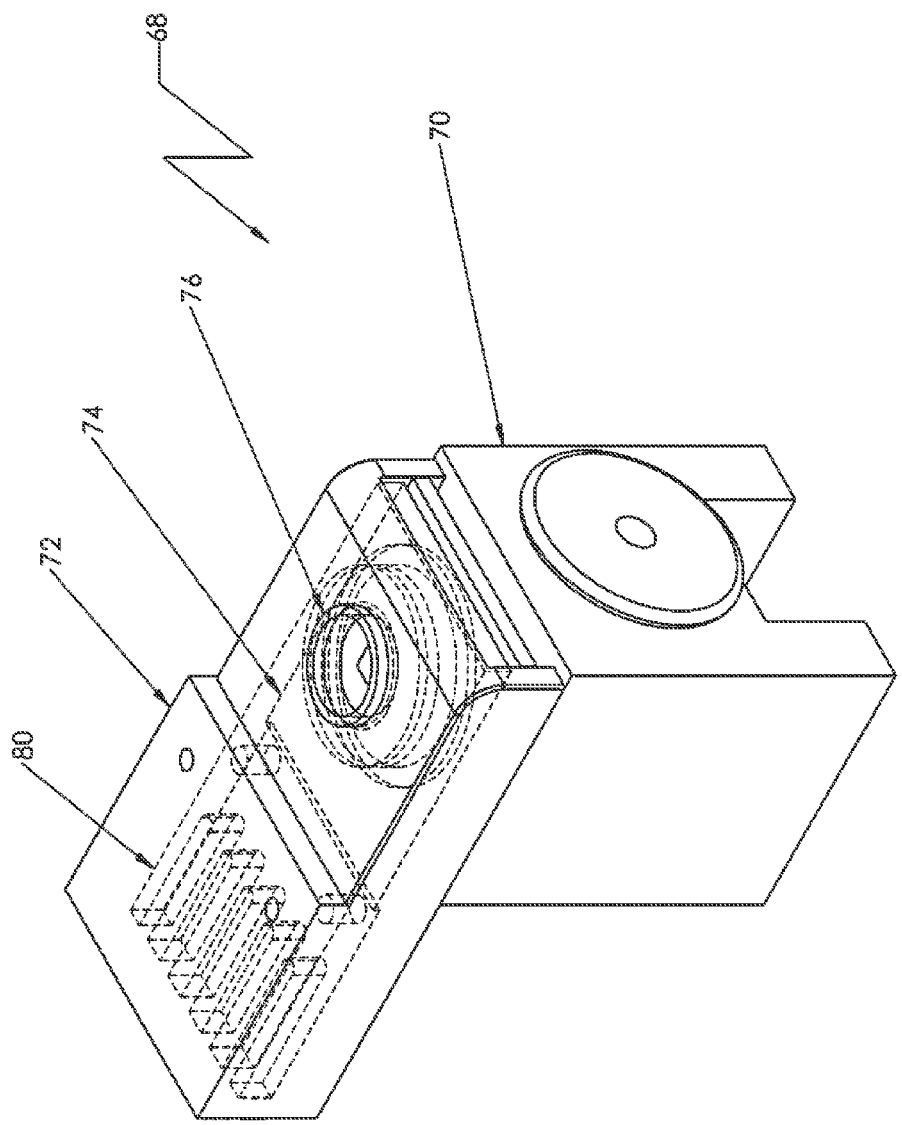
FIG. 6B shows the quad sensor and associated mount.

Also visible through the transparent cover 72 in the view of FIG. 6B is a slotted plate 80 which functions as a heat sink. The transparent cover 72 helps prevent ambient drafts from deleteriously affecting the electrical output signals from the quad sensor 76. Also, as seen in FIGS. 4 and 5 is a plastic shield 82 arranged to surround the light guide member 46 as a way of preventing ambient drafts from altering the outputs from the quad sensor 76.

Figure 2:
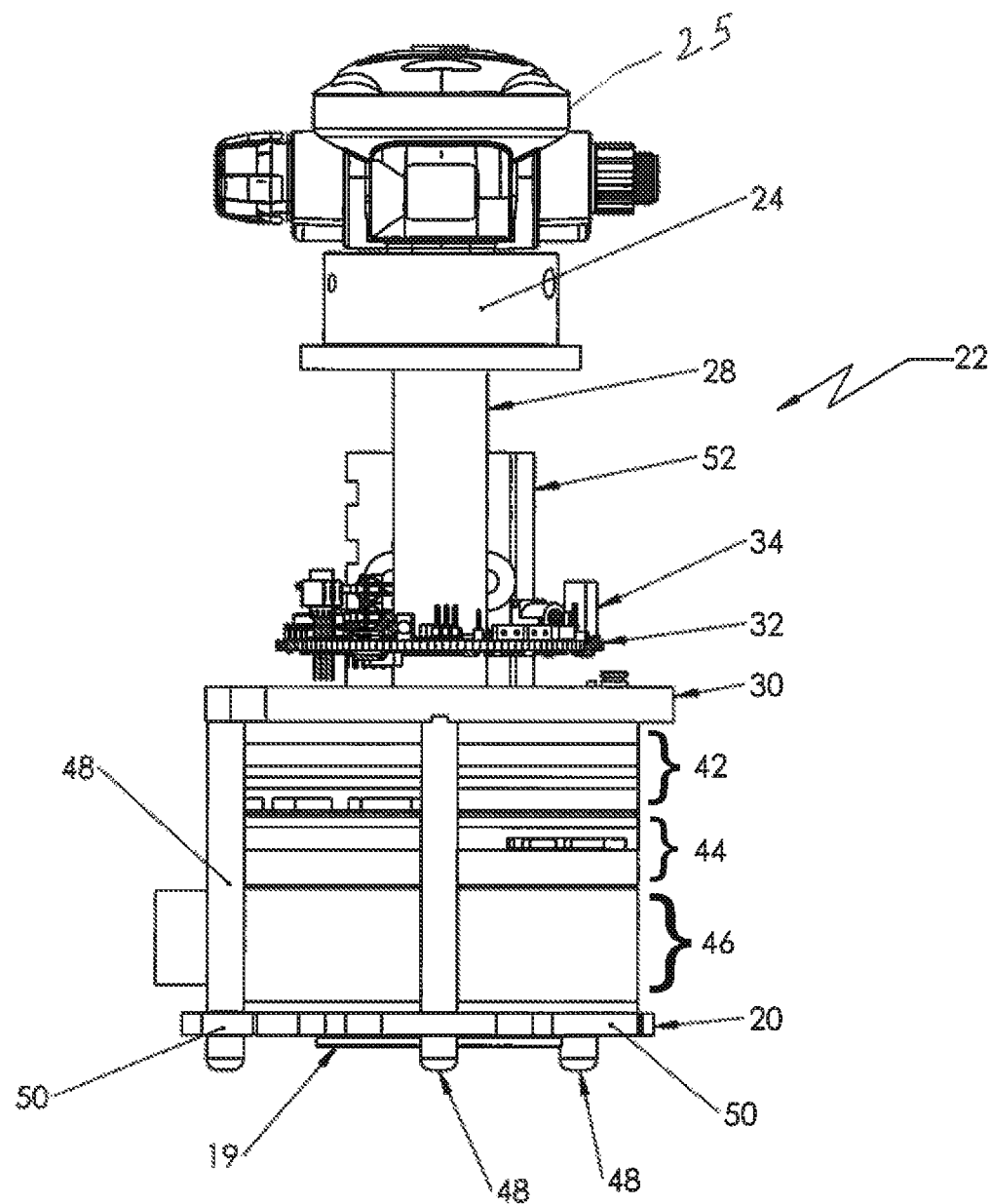
FIG. 2 is a side elevation of a prototype version of the gas analyzer portion of FIG. 1, but with a shroud removed to reveal interior parts.
Figure 7:
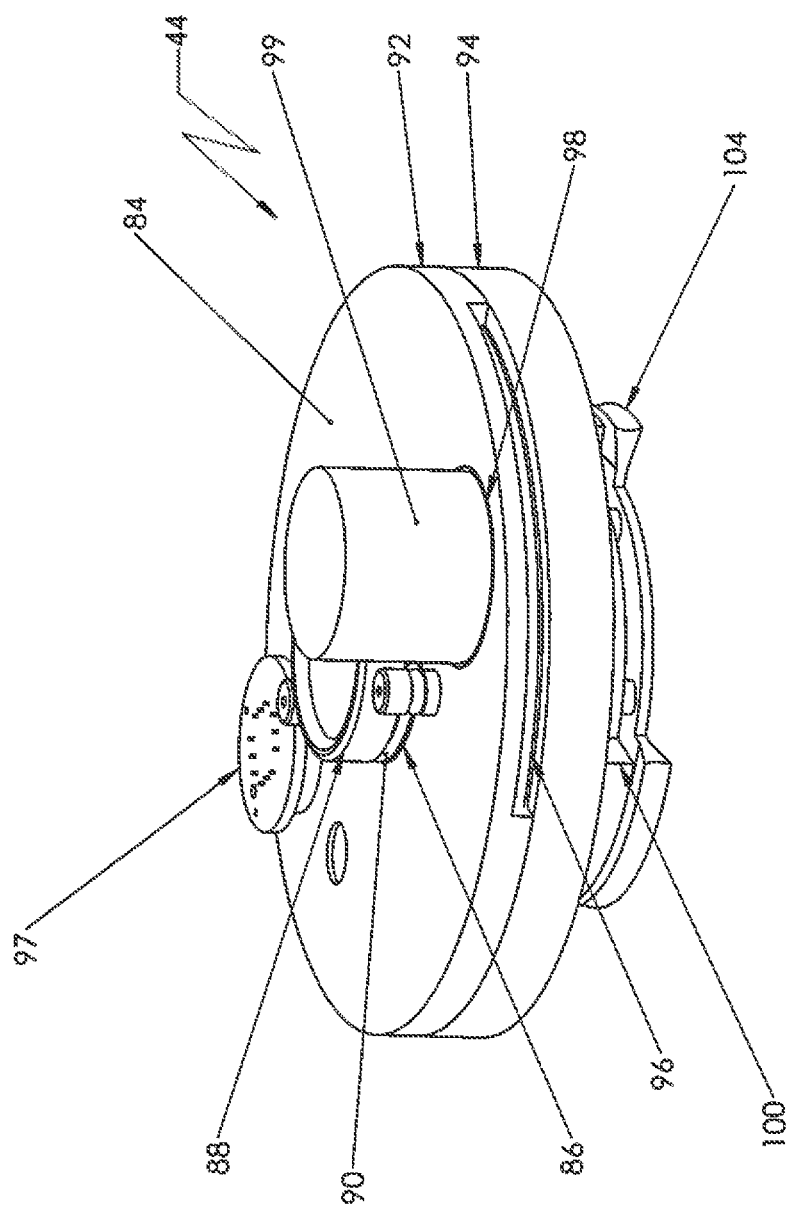
FIG. 7 is a further perspective view of the expire subassembly used in the prototype gas analyzer.
Figure 8:
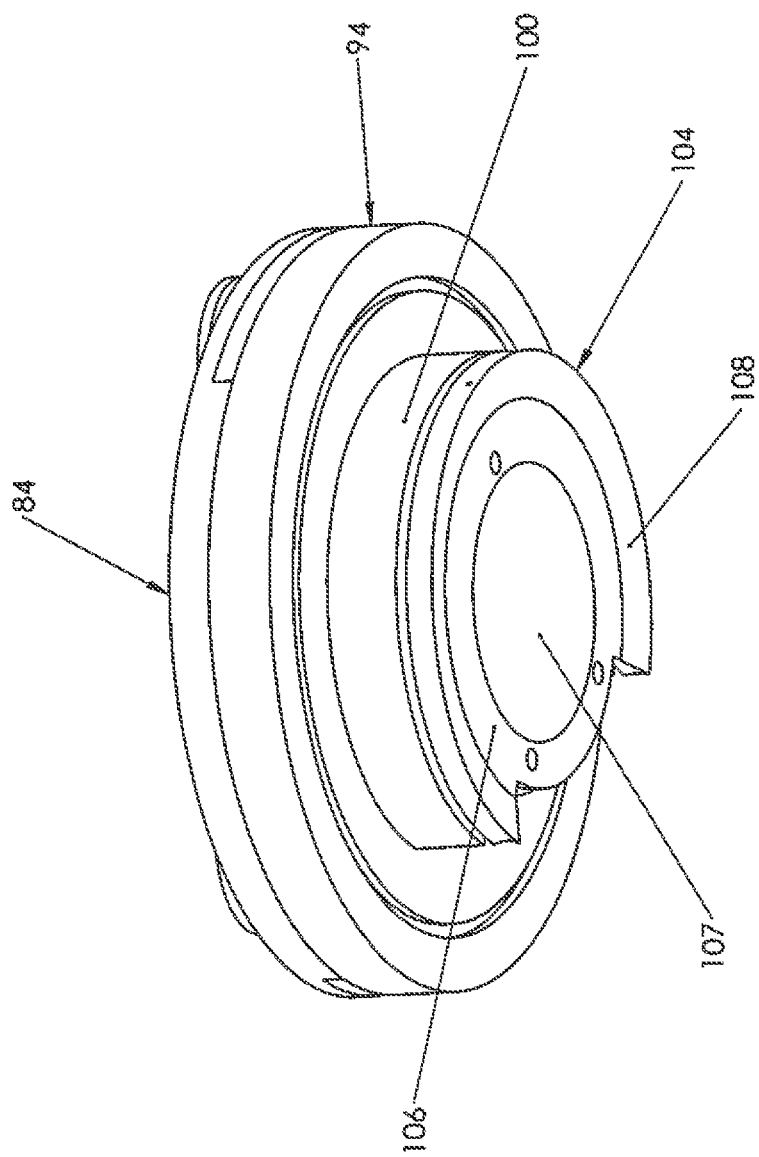
FIG. 8 is a bottom perspective view of the expire subassembly.

Referring next to FIG. 7, there is illustrated an isometric view of the expiratory chamber 44 of FIG. 2. It comprises a top spacer plate 84 having a central aperture 86 through which is fitted an inspire tube 88 that incorporates an O-ring seal 90 thereabout. The top spacer plate 84 has a downwardly depending annular flange 92 which cooperates with a backplane 94 to form a pocket therebetween. A slit 96 is formed through the annular flange 92. Also, a circular bore 98 is formed through the thickness dimension of the spacer plate 84, thus leading to the pocket. Fitted into bore 98 is a commercially available $O_2$ sensing cell 99 which is utilized in performing a nitrogen washout procedure for determining a subject's FRC. At this position, the $O_2$ cell is only exposed to the patient's exhaled breath and is used to measure the concentration of oxygen therein.

Nitrogen washout is a achieved by either measuring the expired nitrogen concentration, which is an expensive analysis, or computing the nitrogen concentration by measuring everything else (primarily $O_2$, $CO_2$ water vapor and argon) in the expired gas. That is to say, by measuring $O_2$, $CO_2$, and water vapor, the only remaining constituent, $N_2$, concentration can be determined.

In FIG. 7, a $CO_2$ sensor 97 fitted through an aperture in the top spacer plate 84. It may comprise a three-channel infrared sensor where the third channel comprises a reference. Integrated with the sensor 97 is a small 3-watt emitter that is separated from the detector by approximately 0.125 inch and disposed within the gap between the spacer plate 84 and the backplane 94 so as to be located in the center of the slit diametrically opposite the oxygen sensor 99. Like oxygen sensor 99, the $CO_2$ sensor 97 is a commercially available modular unit that is inserted into the top spacer plate 84. The expired respiratory gas flow, emitted from a ring of exhaust valves, is evenly distributed between the two sensors 97 and 99. This is important, in that both the $CO_2$ and the $O_2$ changes in the expired gas are integrated with flow to establish instantaneous concentration volume.

Figure 10:
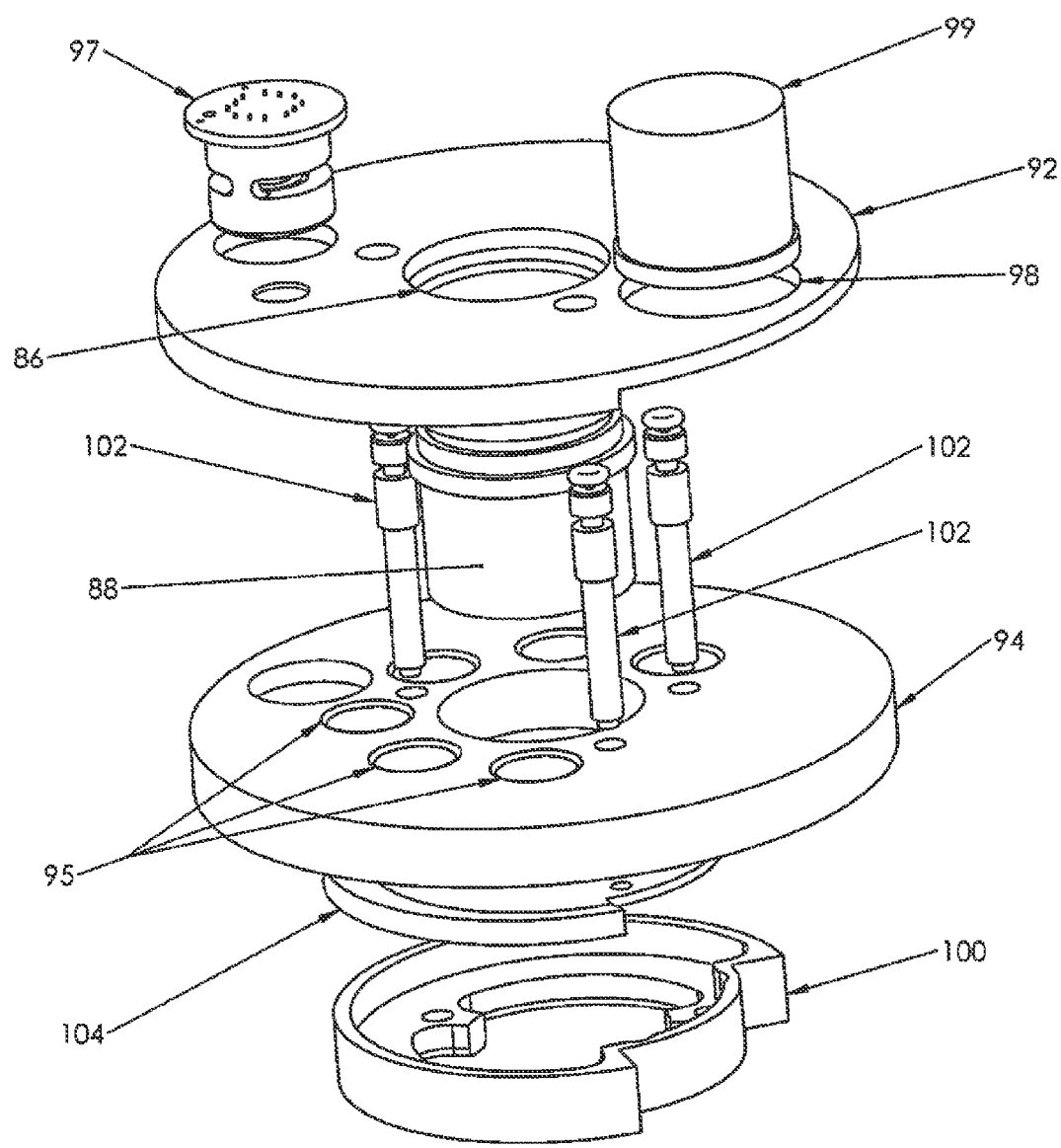
FIG. 10 is an exploded view of the expire subassembly.

Fastened to the undersurface of the backplane 94 is a molded plastic insert 100, the configuration of which is best seen in the view of FIG. 10. Formed through the thickness dimension of the backplane 94 is a plurality of apertures 95 that serve as exhaust ports for expired respiratory gas flow. Each incorporates a leaflet-type, one-way valve providing segregation of inspiratory air/test gas alternate flows and the expirate as will be further elaborated using the schematic diagrams of FIGS. 17A-17D.

In the prototype under discussion, expire assembly 44 is held together by three standoff pins 102 whose lower ends are threaded, allowing them to screw into an impact plate 104 which, because of the particular shape of the standoff pins 102, support the impact plate 104 slightly below the bottom of the plastic insert 100. Two of the three standoff pins 102 are hollow, i.e., they are tubular. One such pin allows for a pressure tap directly ported from the standoff in question into the light guide 46 emerging through a small 0.03 inch hole 111 (FIG. 9) in the impact plate. This is provided to allow measurement of the cell pressure and to correct to Standard Temperature and Pressure (STP) values the gaseous concentrations as per the Gas Laws (0° C. and 1 atm.). The second tubular standoff pin 102 allows for regulated demand gas pressure of about 5 psi to be applied to the proximal "blister" valve 107 whose inflatable elastomeric membrane is affixed to the planar surface 106 on the patient's side of the impact plate. Inflation of blister valve 107 serves to block any expired flow from the patient, such as when the MEP test is being performed.

The outer diameters of the impact plate 104 and the insert member 100 are slightly less than the diameter of the central opening 59 formed in the light guide member 46 (see FIG. 6A) such that the perimeter of the impact plate will reside closely adjacent to the C-shaped groove 64 in the light guide member 46 when the on-airway respiratory gas analyzer 22 is assembled in the manner shown in FIG. 1.

Figure 9:
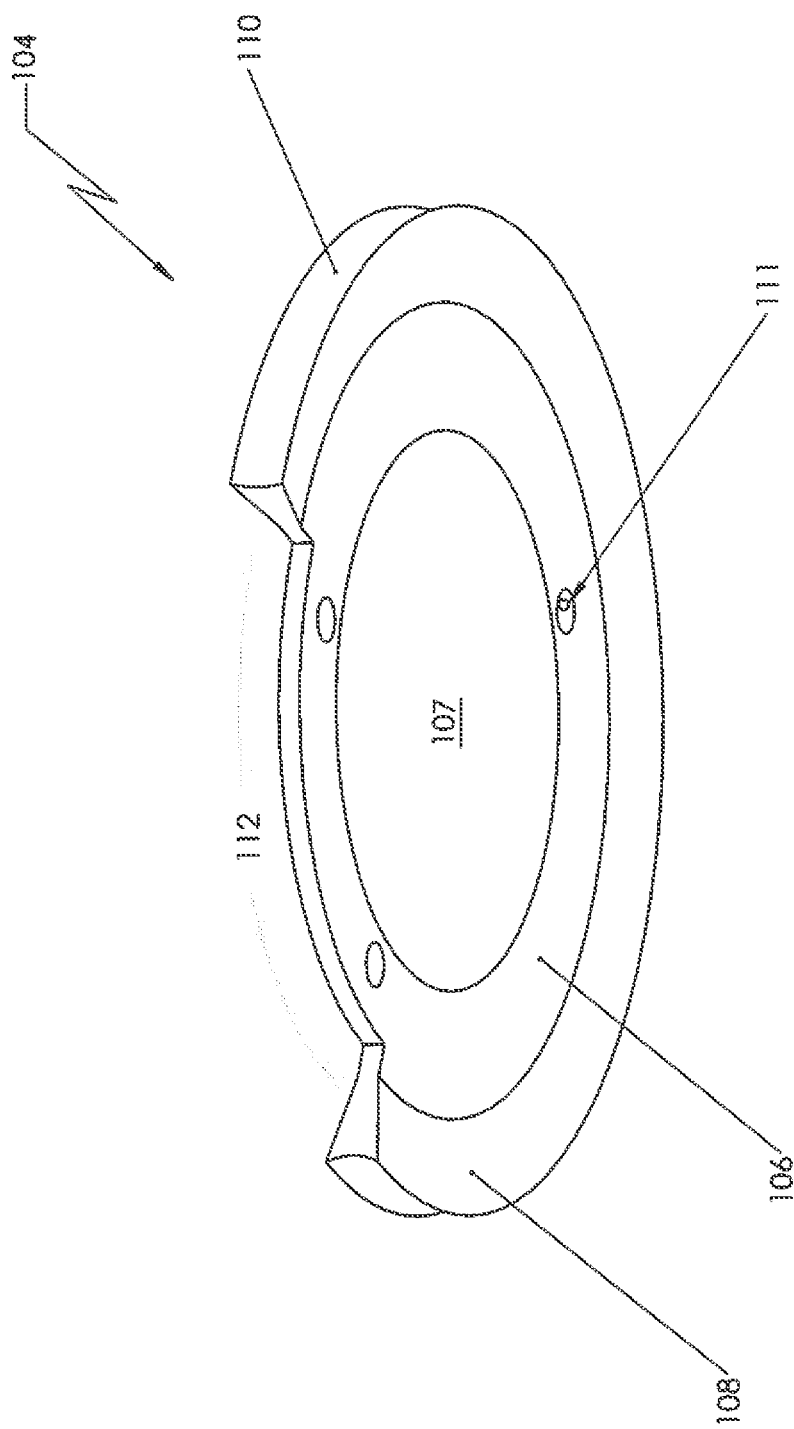
FIG. 9 is a perspective view of an impact plate component.

As shown in the perspective view of FIG. 9, the impact plate 104 has a generally planar central portion 106 and flares in its perimeter portion 108 to an increased thickness dimension and the outer edge of the flared portion 108 is formed so as to exhibit a concave edge 110. The impact plate 104 also has a notch 112 formed inward of the flared portion 108 that aligns with the window 54 of the light guide member 46 for accommodating placement of the light holder assembly 66 and the block 70 that supports the quad sensor 68.

It is the purpose of the impact plate to receive both inspiratory and expiratory respiratory gases thereon and to cause the flow thereof to wash into the highly reflective, non-IR absorbing, C-shaped groove 64 of the light guide member 46 and thereby increase the concentration of the respiratory gases in a zone of the light guide intercepted by light traversing the reflective path to the sensor module. The plate 104 is designed to provide a balance between maximizing the swept volume, yet minimizing back pressure and dead space.

Figure 11:
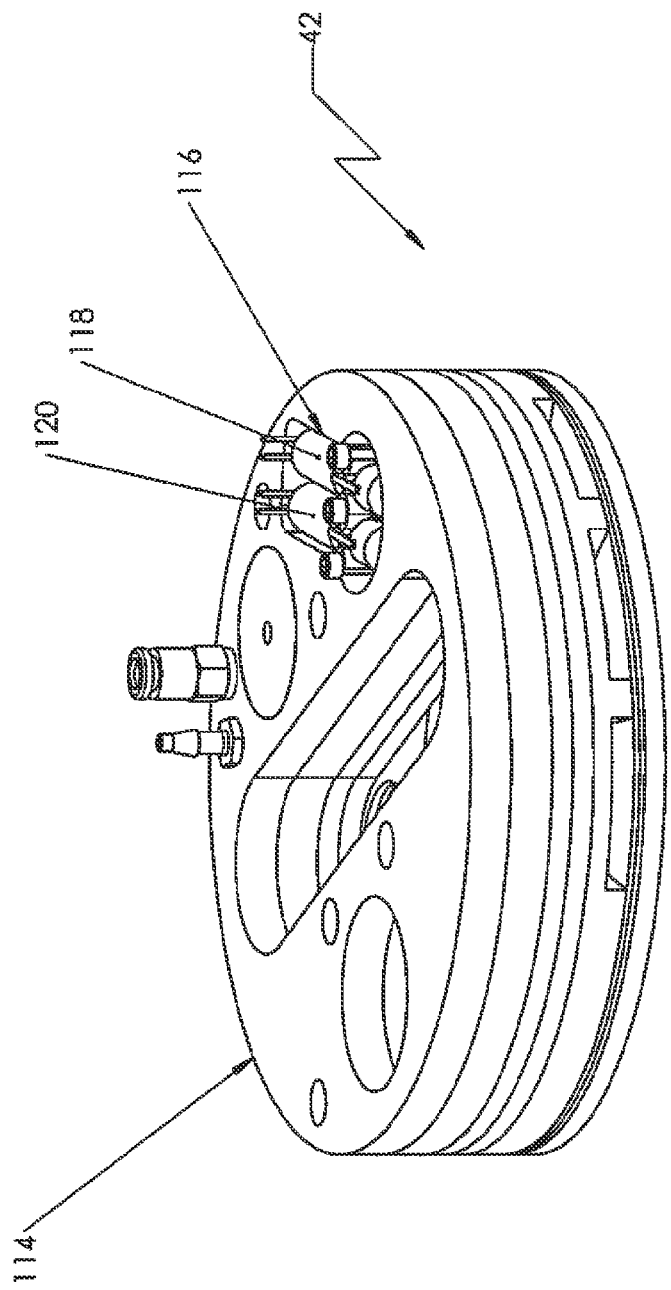
FIG. 11 is a top perspective view of the inspire subassembly.
Figure 12:
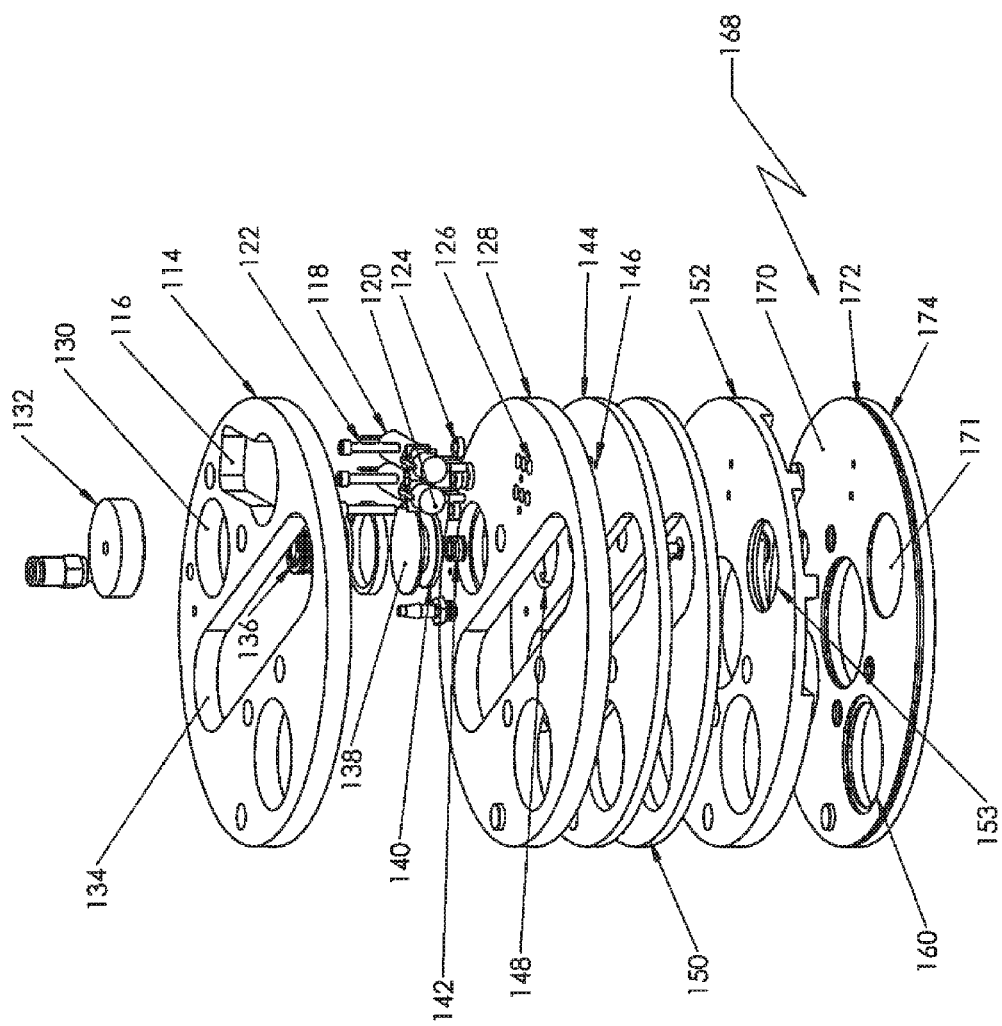
FIG. 12 is an exploded perspective view of the inspire subassembly.

Referring next to FIG. 11, there is shown an isometric view of the prototype inspiratory chamber 42 shown in FIG. 2. It is comprised of a plurality of plates with apertures and grooves formed thereon that when stacked and clamped together thereby provide a composite assembly. The inspire chamber of the prototype has an upper plate 114 having a cavity 116 formed through its thickness dimension in which are fitted first and second solenoid air valves 118 and 120. As seen in FIG. 12, each of the solenoid valves has air inlet tubes 122 and three output tubes, as at 124, that plug into mating apertures, as at 126 on a disk 128 that resides adjacent to the upper disk 114.

Located on the undersurface of the impact plate 104 (FIG. 9) and facing the central aperture of the clamp ring 20 is a proximal valve 107 which we refer to herein as a "blister valve" due to the way it bulges out when inflated by pressurized gas delivered through the solenoid valve 118. It comprises a thin elastomeric disk bonded about its periphery only to the planar surface 106 of the impact plate. The blister valve 107 blocks that aperture to prevent the ability to exhale through the mouthpiece 14. See the schematic diagram of the assembly in FIG. 17. Upon removal of pressure from the blister membrane, the elasticity causes the blister to self-discharge through the solenoid valve 118.

With reference again to the exploded view of FIG. 12, the plate 114 has a cylindrical bore 130 in which is fitted a regulator spring reaction cup 132. Visible through the elongated slot 134 formed through the thickness of the plate 114 is a regulator valve spring 136. It cooperates with a diaphragm retainer 138 and a diaphragm 140 and a further spindle spring 142 to form a pressure regulator assembly 143 (FIG. 17) to further reduce the pressure provided at the output of the scuba demand valve associated with a tank of high pressure gas from about atmospheric pressure to a lower value of about 5 psi for actuating "blister valves" disposed in the inspiratory chamber 42 and on the impact plate 104 without causing them to rupture.

Disposed beneath the disk 128 is a further disk 144, the undersurface of which includes grooves extending from apertures as at 146 which are associated with the outlet ports 124 of the solenoid valves 118 and 120. The grooves (not shown in FIG. 12) extend and intersect with an aperture 148 that receives the regulator valve assembly 143 comprising the parts 132, 136, 138, 140 and 142 therein.

Figure 13:
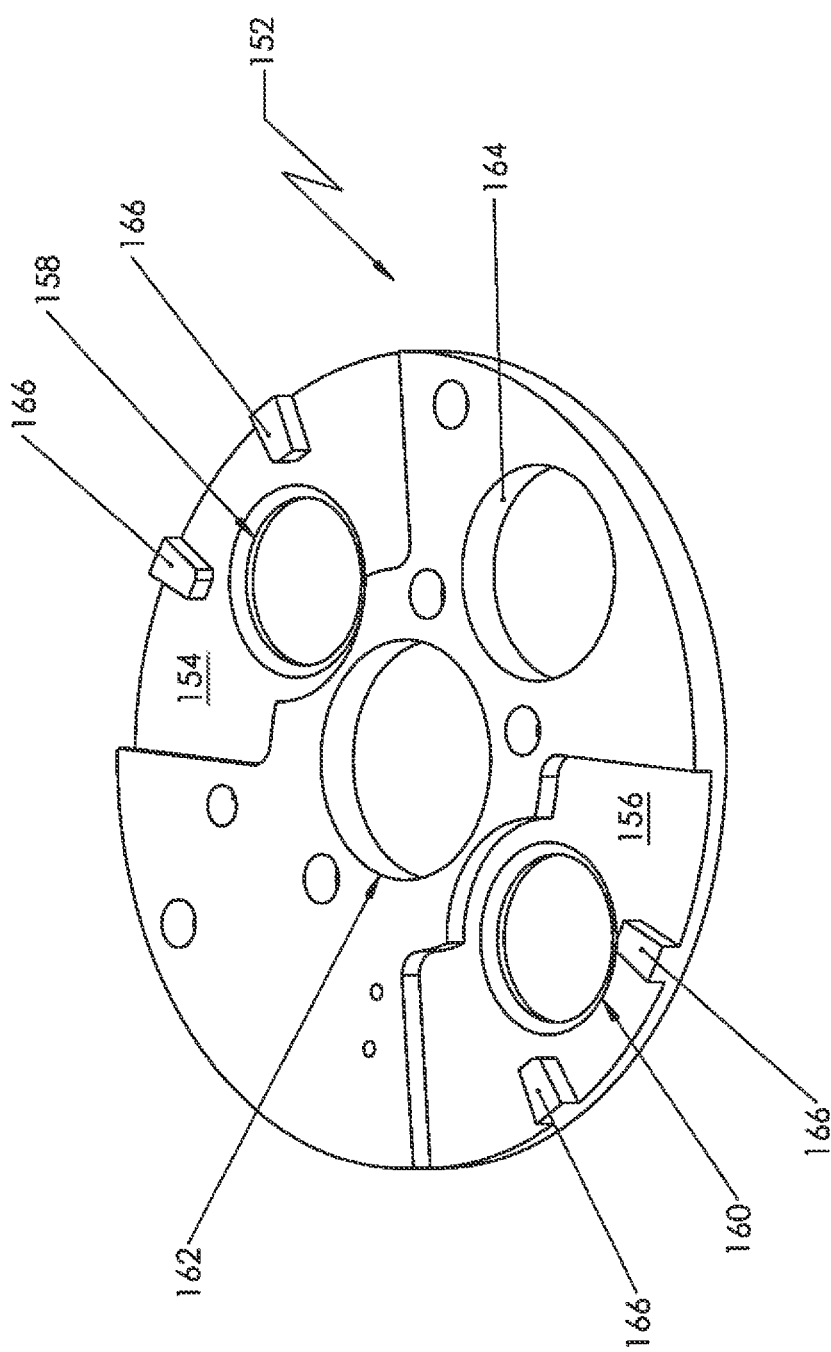
FIG. 13 is a perspective view showing the obverse side of the end disk of the inspire chamber.
Figure 14:
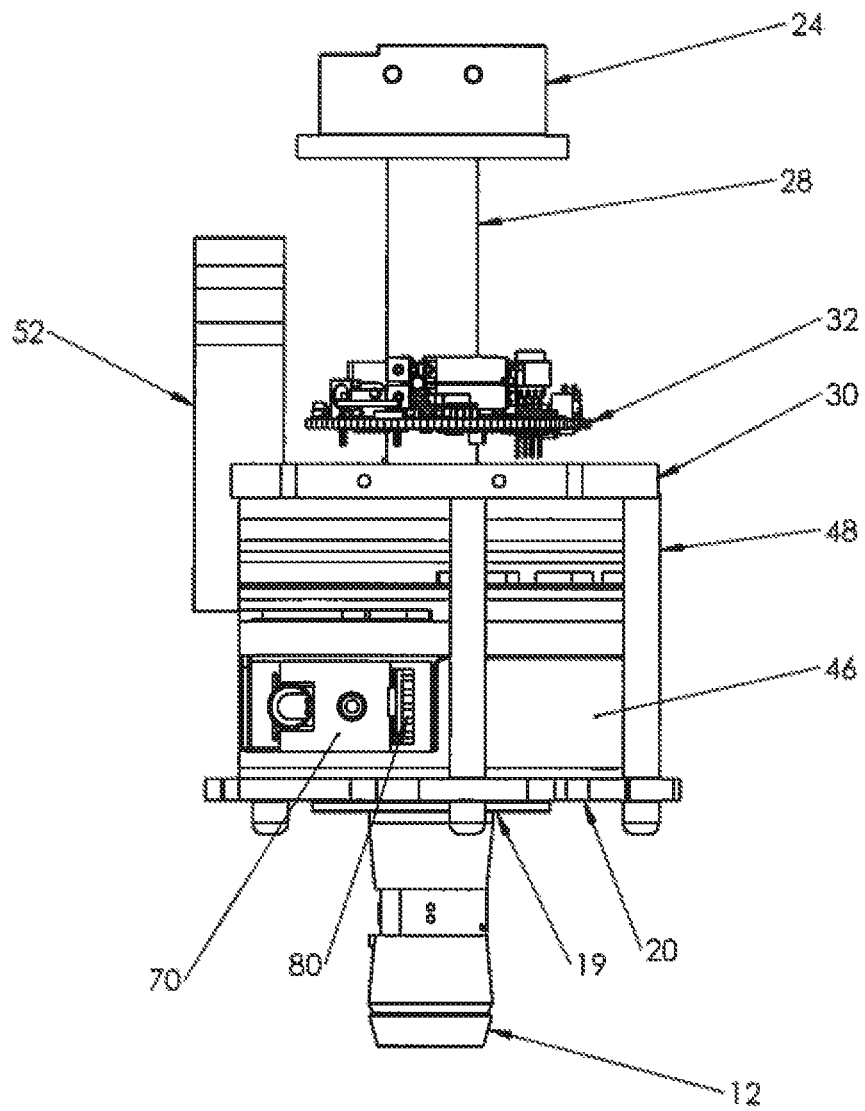
FIG. 14 is a side elevation of the respiratory gas analyzer showing how the optical sensor is mounted with respect to the light guide member.
Figure 15:
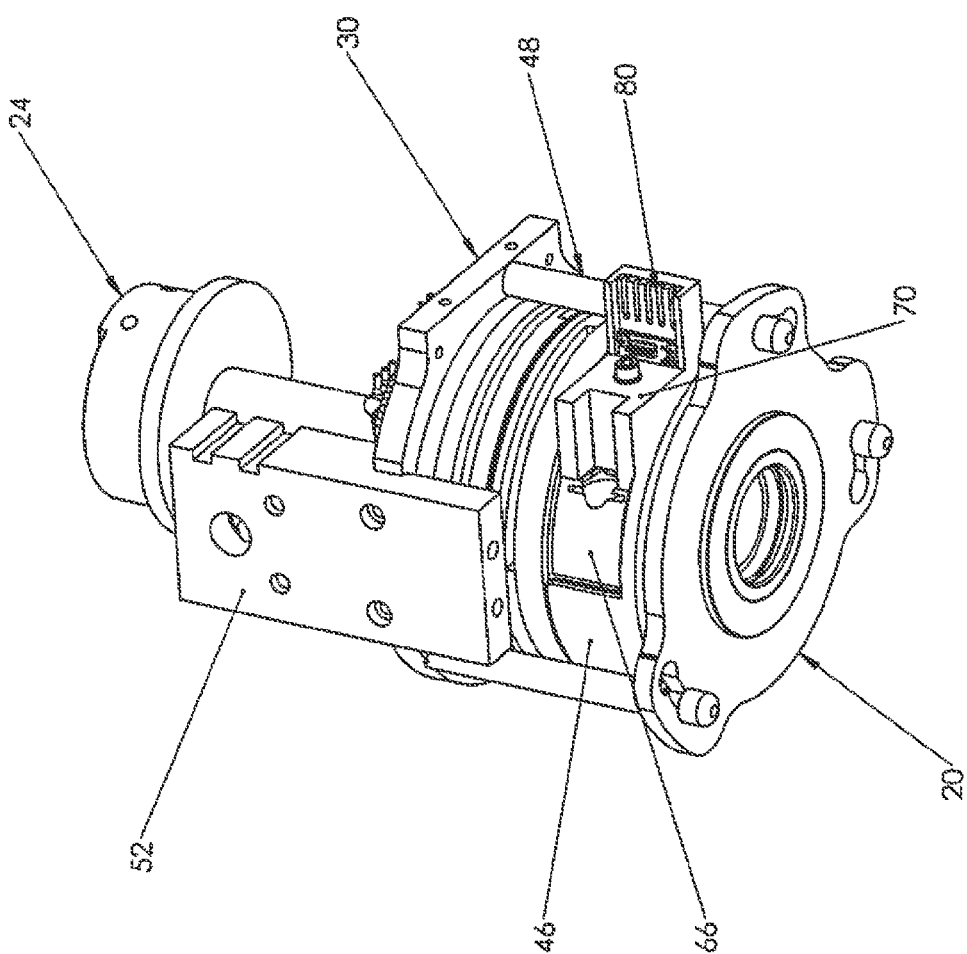
FIG. 15 is a perspective view showing the sensor module cooperation with the light guide member.

Beneath the flat disk 144 is a further flat disk or spacer 150 having a hole pattern similar to that of disk 128 except for the aperture 148. Next in line in forming the inspire chamber is a disk 152 which is somewhat thicker than the spacer 150 and which has formed on its undersurface generally trapezoidal-shaped recesses 154 and 156 encompassing circular apertures 158 and 160 (FIG. 13). The center aperture 162 and the further aperture 164 extend through the entire thickness dimension of the disk 152. Spacing pedestals, as at 166, prevent bending or deflection of the thinner trapezoidal segments 154 and 156 as the clamping tie rods 48 are secured.

Completing the inspire chamber assembly is a inspire blister valve assembly 168. It comprises a sandwich combination of an upper inspire blister diaphragm support plate 170, an intermediate polyurethane diaphragm layer 172 and an inspire blister valve plate 174.

When the solenoid air valve 118 is appropriately actuated by electrical control signals provided by the on-board electronics on the printed circuit board 32 shown in FIG. 5, test gas is delivered from a high pressure supply tank, through a scuba demand valve and the pressure regulator assembly 36 described above to distend the blister diaphragm 172 so as to occlude adjacent ports 158 and 160 and thereby prevent the patient from inhaling ambient air while instead drawing gas from the supply tank (not shown).

Figure 16:
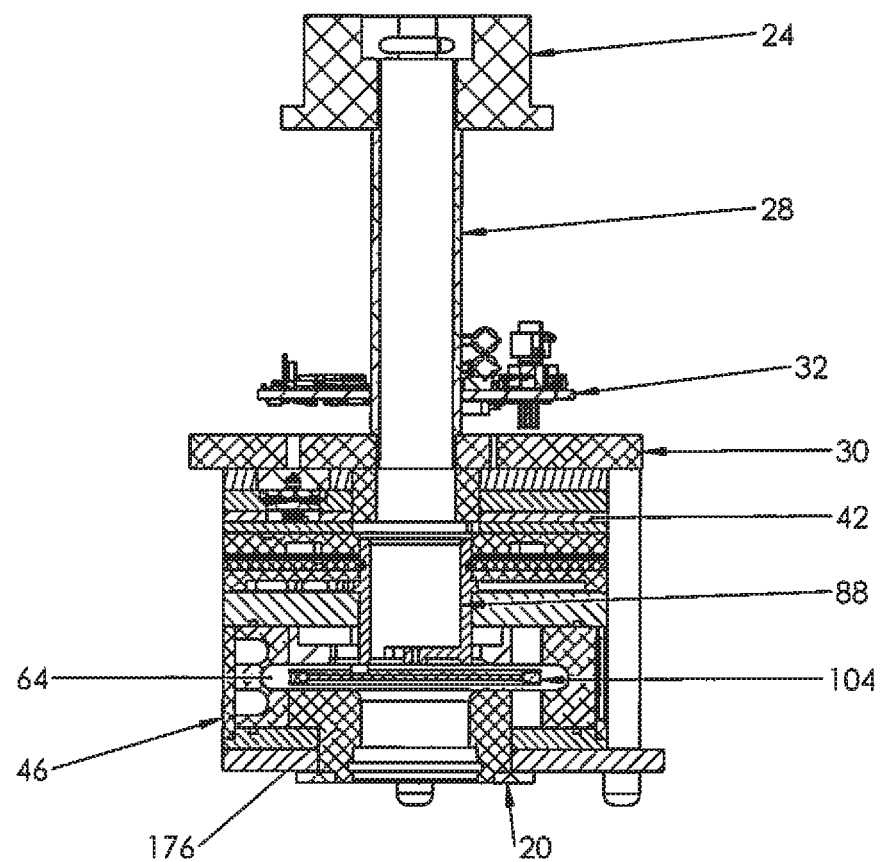
FIG. 16 is a longitudinal cross-sectional view of the respiratory gas analyzer.

As can be seen in the cross-sectional view of FIG. 16, the adaptor plate 20 comprises an integrally-formed tubular stub 176 leading to the C-shaped groove 64 of the light guide 46 and closely adjacent to the proximal blister valve diaphragm on the under surface of the impact plate 104. Furthermore, as observed in FIG. 16, the scuba demand valve adaptor 24 is affixed to the upper end of the tube 28 whose lower end passes through a central opening in each of the members comprising the manifold mounting plate member 30 and the several plates comprising the inspiratory chamber 42 where it forms a sealed joint with the inspire tube 88 whose lower end also terminates in the highly polished reflective groove 64 of the light guide member 46.

From what has been described, those skilled in the art can appreciate that when a subject is allowed to exhale, the respiratory gasses will flow through the pneumotach 12 to measure the flow, all as more particularly explained in the aforereferenced Norlien et al. '773 patent and with that exhaled breath, impinging upon the impact plate 104 that serves to divert a breath sample into the C-shaped groove 64 that extends between a IR light source and the quad detector 76. The quad detector is provided with optical filters having pass bands associated with the spectral intensity of one or more of carbon monoxide, carbon dioxide and methane. The fourth detector is used as a reference so, for example, after the infrared light passes through the circular sample chamber of the light guide, radiation is absorbed by the presence of, say, $CO_2$ and the unabsorbed radiation impinges upon the photodetector. Because $CO_2$ absorbs infrared radiation, the greater the concentration of carbon dioxide in the sample, the less infrared light that will arrive at the detector. Thus, variations in the concentration of $CO_2$ alter the electrical output signal of the detector. The same holds true for the elements of the quad detector having filter elements for detecting CO and $CH_4$.

In the past, so-called infrared capnometers have used linear sample chambers dictating a form factor for a sensor module that is unduly bulky. By providing a sample chamber in the form of a circular segment, a sample chamber of an effectively greater length can be achieved, which improves the sensitivity of the gas constituent measurement. Also, by combining the arcuate sample chamber with the impact plate of the present invention, the concentration of inspired and expired gas samples results in a greatly improved measurement apparatus in a more compact form factor.

Having described the constructional features of the on-airway pulmonary function tester, consideration will next be given to its mode of operation in conducting two classical PFTs, namely the diffusing capacity of the lungs ($D_{LCO}$) and FRC by way of $N_2$ washout. Here, reference will be made to the schematic drawings of FIGS. 17A-17D.

The single-breath diffusing capacity test is the most common way to determine diffusion capacity. The test is performed by having the patient expire all of the air that he or she can, leaving only the residual lung volume of gas. The patient then inhales a test gas mixture rapidly and completely, reaching the total lung capacity as nearly as possible. This test gas mixture contains a small amount of carbon monoxide (usually 0.3%) and a tracer gas (methane 0.3%) that is freely distributed throughout the alveolar space, but which does not cross the alveolar-capillary membrane. Methane is one such gas. Helium is another. The test gas is held in the lung for about 10 seconds, during which time the CO (but not the methane) continuously moves from the alveoli into the blood. The subject then exhales. The first 500 to 1,000 ml of the expired gas is disregarded and the next portion which contains gas that has been in the alveoli is analyzed. By analyzing the concentration of carbon monoxide and inert gas in the inspired gas and in the exhaled gas, it is possible to calculate $D_{LCO}$ as the volume of CO taken up by the lung divided by the partial pressure of CO in the alveoli.

Figure 17A:
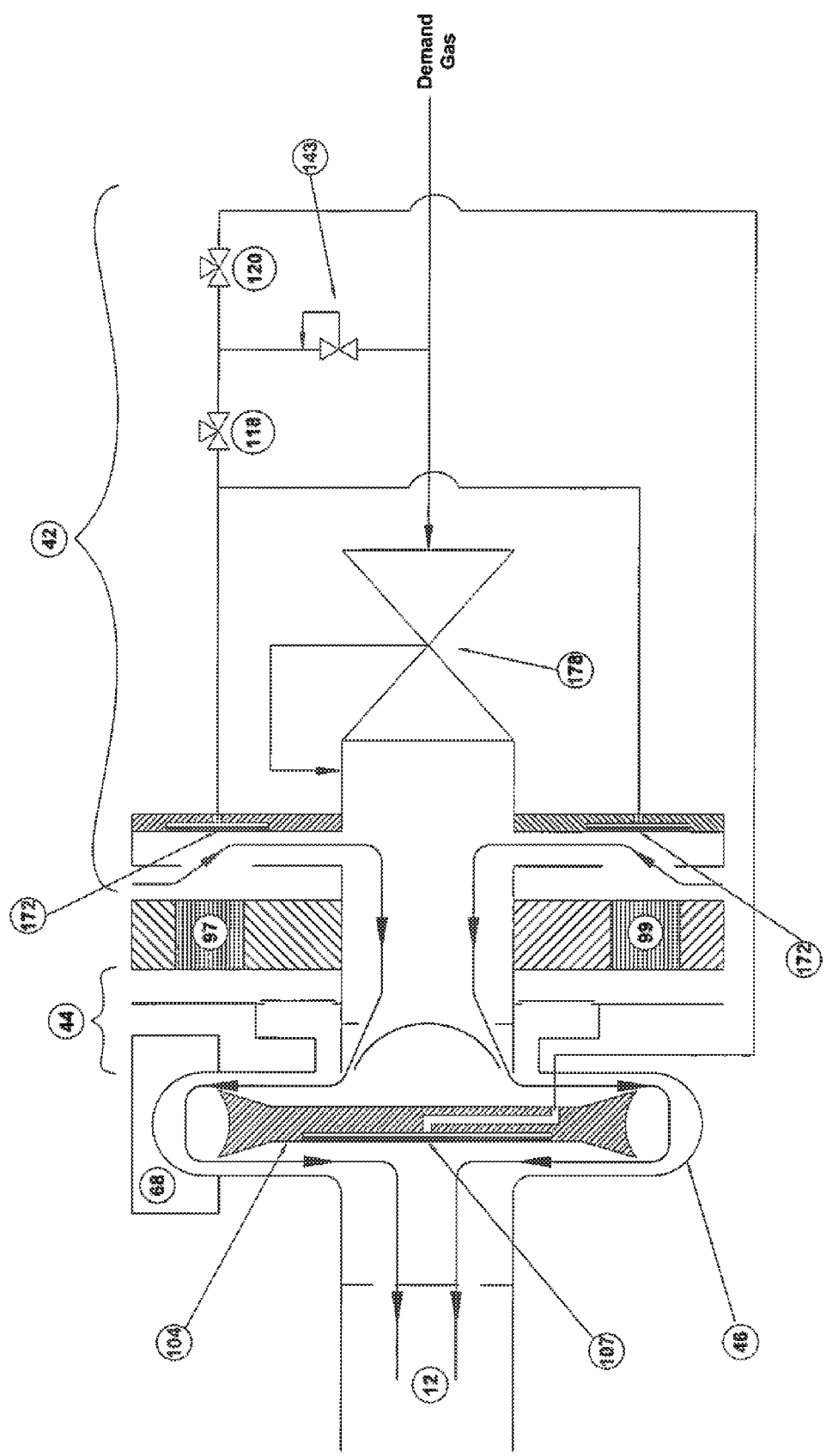
FIG. 17A is a schematic drawing of the respiratory gas analyzer in an ambient air inspire mode.
Figure 17B:
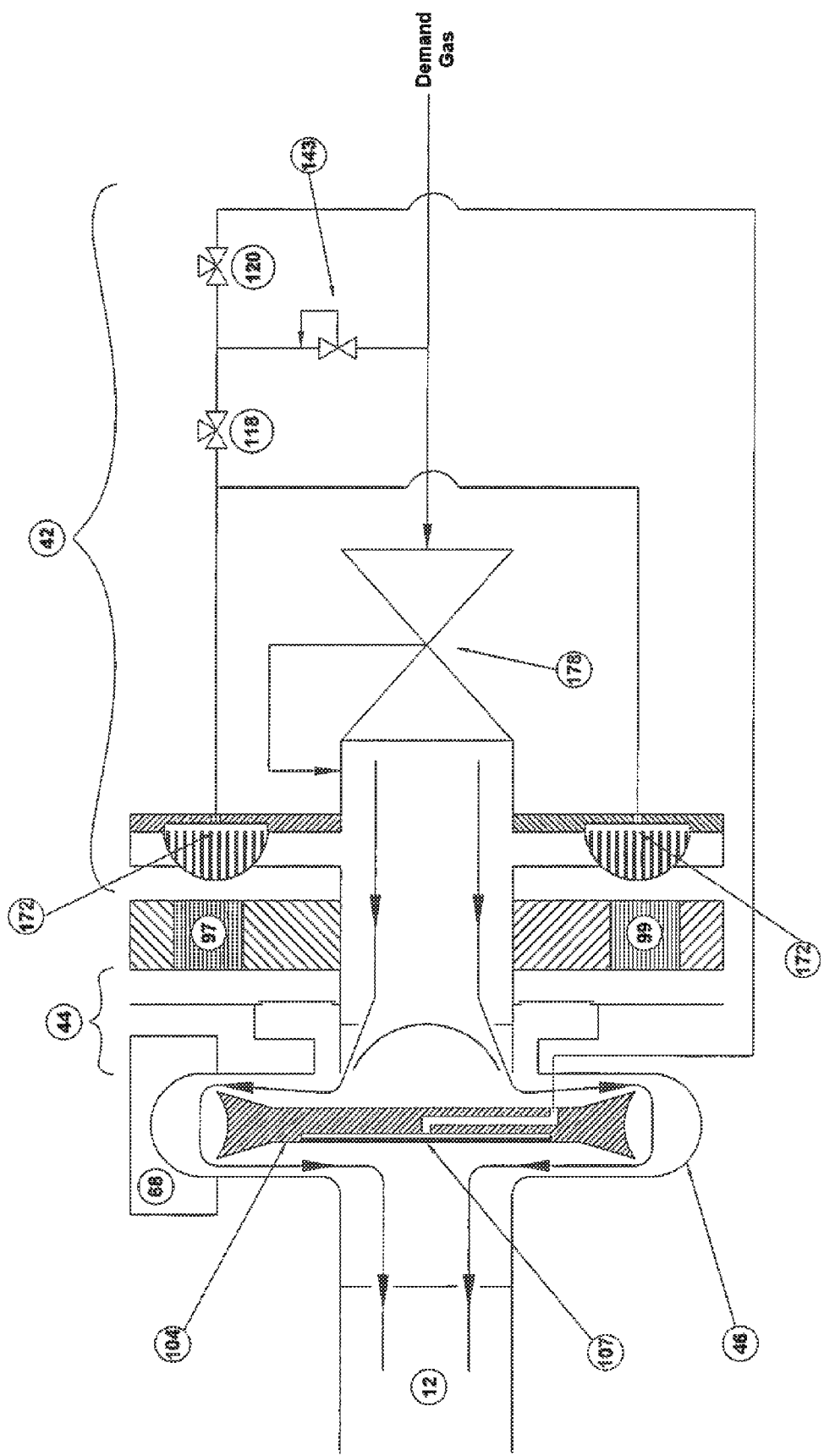
FIG. 17B is a schematic diagram illustrating the state of the valving upon inspiration of the demand gas.
Figure 17C:
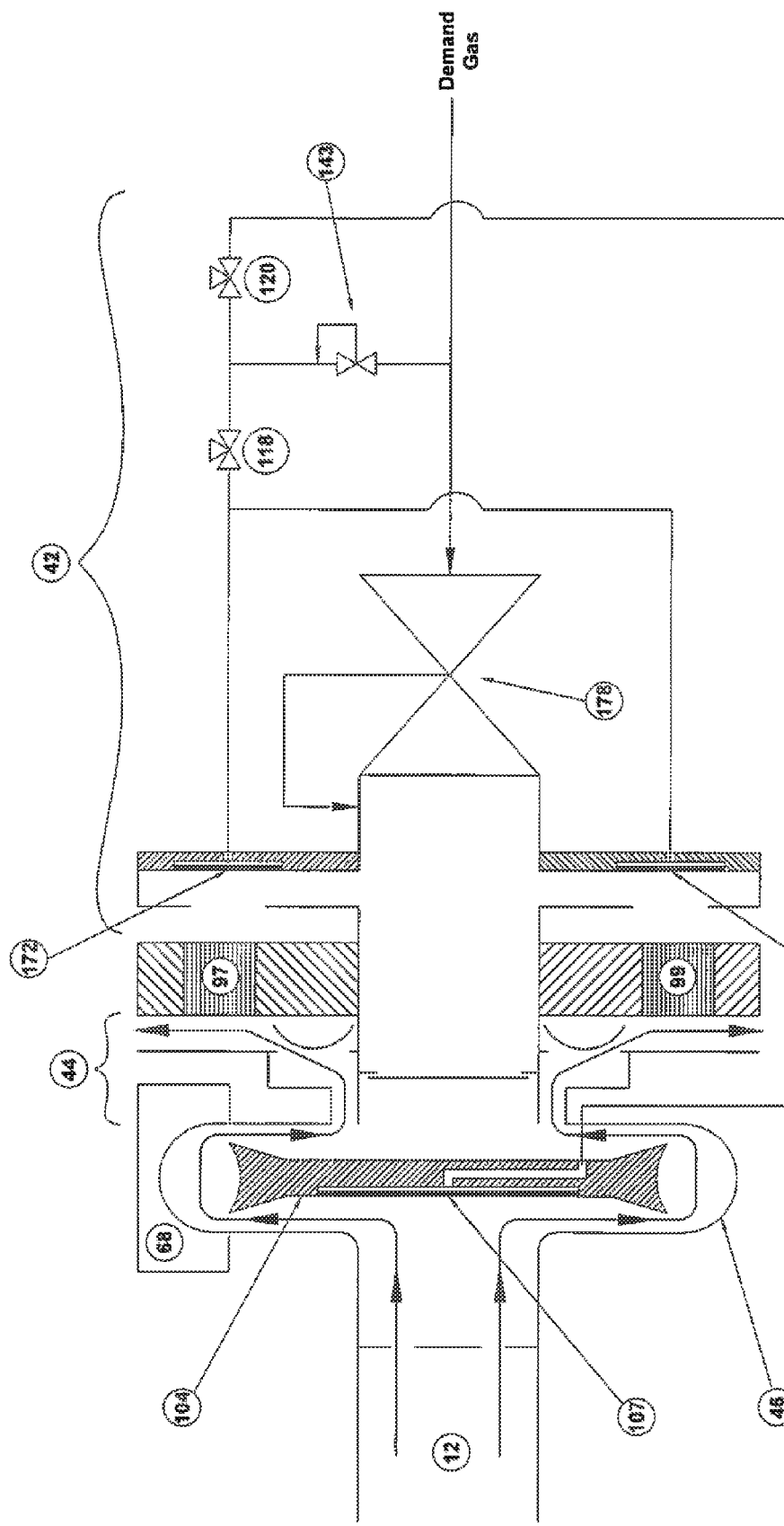
FIG. 17C is a schematic diagram illustrating the state of the valving upon expiration.
Figure 17D:
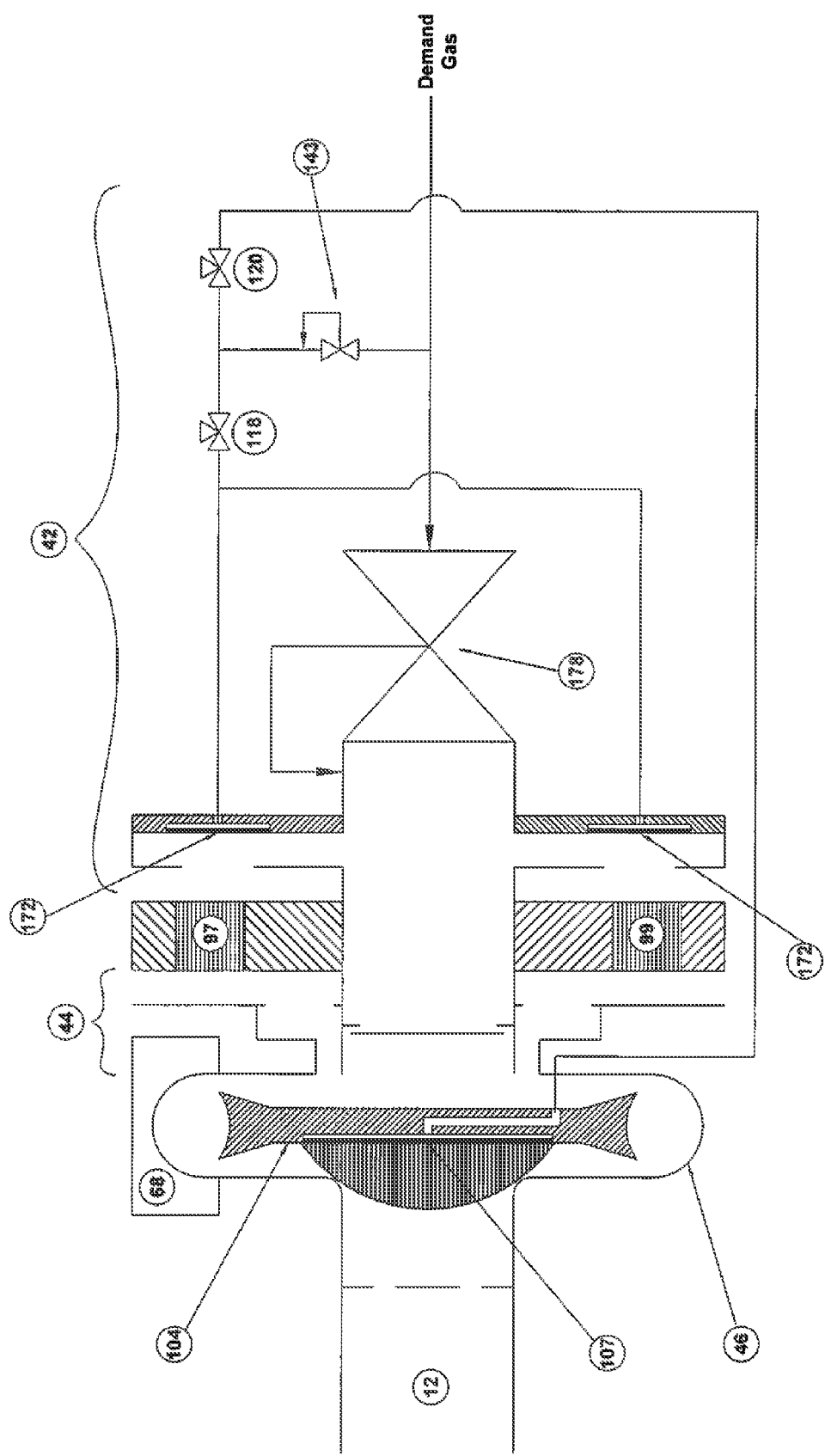
FIG. 17D is a schematic diagram illustrating the state of the valving during a BMEP test and during a stage3 of the DLCO test where exhalation is prevented.

In practice, the assembly depicted in FIG. 1 is suspended from a spring-loaded articulated arm to position the mouthpiece 14 of the pneumotach directly in front of the patient's mouth when the patient is seated or standing. The patient then places the mouthpiece in his or her mouth and a nose clip is applied to prevent breathing through the nasal passages. Normal ambient air breathing takes place. Then, solenoid 120 is actuated and demand gas flows as shown in FIG. 17B when the blister valves 172 expanded to block entry of ambient air. At this time, a test gas mixture of the type described is coupled through a scuba demand regulator valve to the adaptor 24. The person then inhales the test gas mixture rapidly and as completely as possible as indicated by the directional arrows in FIG. 17B. During inhalation, the scuba demand valve 178 (FIG. 17A) opens to allow the test gas to flow down the tube 28 through the aperture 86 in the plate member 92 (FIG. 10) and through the central aperture of the backing plate 94, across the impact plate 104 and ultimately through the tubular stub 176 of the adaptor plate 20 and the lumen of the pneumotach into the patient's lungs. Upon completion of the deep inhale, a control signal is delivered to the solenoid valves 120 causing pressurized gas to inflate an elastomeric 110 diaphragm 107 covering an aperture in the expiratory chamber 44 which rises as a result to block the aperture 21 in the adapter 20 to thereby block the patient's effort to exhale for a predetermined time interval, e.g., 10 seconds. See FIG. 17D. At the end of this interval, the blister valve is depressurized and allowed to reopen, allowing expired breath to pass upward through the expire chamber 44 and out through the leaflet valves occupying apertures 95 in the plate 94 to the ambient. See FIG. 17C. After a first predetermined volume of breath has been exhaled, the quad detector output is captured, yielding a signal proportional to the concentration of CO gas in the expired flow traversing the light guide, thereby permitting DLCO to be computed.

Nitrogen washout is a PFT for measuring dead space in the lung during a respiratory cycle, as well as some parameters related to the closure of airways. In performing this test, the subject is made to breathe a mixture of high $O_2$ content to wash out the resident $N_2$. Since $N_2$ constitutes approximately 80% of the lung gases, collection of all the exhaled gas and determination of the volume of $N_2$ permits calculation of lung volume, provided that the initial $N_2$ concentration in the lungs, the $N_2$ concentration in the exhaled volume and the total exhaled volume are known.

Most modern $N_2$ washout systems integrate $N_2$ concentration and expiratory flow on a breath-by-breath basis and the volume and concentration of each exhaled breath are measured separately and stored in a memory. The sum of the volumes and the weighted average of the nitrogen concentration are calculated by a computer.

Wearing nose clips, the patient breathes 100% oxygen until nearly all of the nitrogen has been washed out of the lungs, leaving less than 2.5% nitrogen therein. When the peak exhaled concentration of nitrogen is less than this 2.5% value, the patient exhales completely and the fractional concentration of alveolar nitrogen is noted.

To calculate FRC or TLC by the nitrogen washout technique, several measurements must be made. These include the total volume of gas exhaled during the test ($\dot{V}_E$), the fractional concentration of exhaled nitrogen in the total gas volume ($FEN_2$), the fractional concentration of nitrogen in the alveoli at the end of the test ($FAN_2$). The FRC can be calculated with the following equation:

$$FRC=(\dot{V}_E) \times (FEN_2) + (0.78 - FAN_2)$$

Using the on-airway pulmonary function tester of the present invention, the patient first breathes in and out normally through the mouthpiece of the pneumotach such that the concentration of nitrogen in the subject's lungs is approximately 78%, i.e., the ambient level. At the start of the test, control signals from a microprocessor/microcontroller are applied to the solenoid valve 120, causing gas, the pressure of which is regulated by the regulator assembly 138 and 140 (FIGS. 12 and 17) to flow to blister valves 171 on the support plate 170 to distend the elastomeric diaphragm 172 to the point where it occludes the aperture 153 on the disc 152 to block entry of ambient air so that during inhalation, pure oxygen is drawn from a tank (not shown) through the scuba demand valve 178 and down through the low volume tube 28 and the expire tube 88 and through the pneumotach 12 into the subject's lungs. During exhalation, flow and therefore volume measurements are derived from the pneumotach 12 and the concentration of nitrogen therein is measured until such time as the 2.5% level nitrogen in the lungs is reached with the weighted average of the nitrogen of each breath being calculated. See FIG. 17C.

It should be noted that since the FRC measurement is permanently integrated with DLCO measurement, the need to measure $CO_2$ concentration in the DLCO test is eliminated as the $CO_2$ measurement from the FRC can be imported into software to correct for the minor interference that $CO_2$ causes in the CO measurement. This makes it unnecessary for the quad sensor to measure $CO_2$ allowing a channel to measure acetylene as well as methane.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. A mainstream respiratory gas analyzer apparatus comprising:
   a. a pneumotach having a mouthpiece at a proximal end;
   b. a gas analyzer assembly removably mounted on a distal end of the pneumotach, the gas analyzer assembly having:
      i. a body having fluid passageways allowing one of a test gas or ambient air to be inspired and expired through the pneumotach;
      ii. a toroidal light guide contained in said body and having a central opening, an interior side wall of the toroidal light guide defining the central opening, the side wall including a groove of an arcuate contour coated with a light reflective non-IR absorbing material;
      iii. an IR emitter aligned with one end of the groove and an IR sensor aligned with an opposed end of the groove and coupled to a microprocessor adapted to receive signals relating to concentrations of respiratory gases and constituents of test gases;
      iv. a circular impact plate having a planar central portion tapering to an increased thickness about a periphery thereof disposed in the central opening of the toroidal light guide and centered in non-contact relation with respect to the groove, the outer edge of the impact plate having a concave recess for diverting expired respiratory gas flowing through the pneumotach into the groove, the impact plate being symmetrical about a central plane to also serve to divert a test gas being inspired into the groove;

v. a pneumatically activated blister valve disposed on the central portion of the impact plate and cooperating with a passageway in the body leading from a pressurized gas supply to said blister valve for selectively blocking and unblocking expiratory gas flow from the gas analyzer.

2. The mainstream respiratory gas analyzer apparatus of claim 1 wherein the groove is generally C-shaped in cross-section.

3. The mainstream respiratory gas analyzer apparatus of claim 1 and further including:
   a. an adapter plate for removably coupling the body of the gas analyzer assembly to one end of the pneumotach; and
   b. an adapter sleeve adapted to couple the gas analyzer assembly to a tank of test gas through a scuba demand valve.

4. The mainstream respiratory gas analyzer apparatus of claim 1 and further including a solenoid air valve disposed in the passageway for controlling operation of the pneumatically activated blister valve.

5. The mainstream respiratory gas analyzer apparatus of claim 1 wherein the IR emitter is an incandescent bulb and the IR sensor is responsive to IR energy.

6. The mainstream respiratory gas analyzer apparatus of claim 5 wherein the incandescent bulb is positioned in proximity to the groove to thereby supply heat energy to the light reflective material sufficient to prevent vapor condensation thereon.

7. The mainstream respiratory gas analyzer apparatus of claim 5 wherein the IR sensor includes a plurality of sensor elements, each sensor element incorporating a filter having pass bands characteristic of one of $CO$, $CO_2$ and $CH_4$ and a further sensor element serving as a reference.

8. The mainstream respiratory gas analyzer apparatus as in claim 1, wherein the body of the gas analyzer assembly includes at least one valve which when open permits ambient air to be inhaled and exhaled through the pneumotach and when closed allows only the test gas to be inhaled through the pneumotach.

9. The mainstream respiratory gas analyzer apparatus as in claim 8, wherein the IR sensor measures the concentration of $N_2$ in said groove of each breath exhaled through the pneumotach when the at least one valve is closed.

10. The mainstream respiratory gas analyzer apparatus as in claim 9 and further including means for storing the measured $N_2$ concentration values of a series of successive exhaled breaths following the closure of the at least one valve.

11. The mainstream respiratory gas analyzer apparatus as in claim 10, wherein the at least one valve comprises a pneumatically expandable diaphragm for selectively blocking and unblocking a passageway in said body.

12. The mainstream respiratory gas analyzer apparatus as in claim 11, wherein the test gas is $O_2$.

* * * * *